US010888521B2

(12) United States Patent
Chen et al.

(10) Patent No.: US 10,888,521 B2
(45) Date of Patent: Jan. 12, 2021

(54) SUSTAINED RELEASE COMPOSITIONS USING WAX-LIKE MATERIALS

(75) Inventors: Andrew Xian Chen, San Diego, CA (US); Patricia D. Kigin, Scottsdale, AZ (US)

(73) Assignee: Farnam Companies, Inc., Phoenix, AZ (US)

(*) Notice: Subject to any disclaimer, the term of this patent is extended or adjusted under 35 U.S.C. 154(b) by 1181 days.

(21) Appl. No.: 12/040,443

(22) Filed: Feb. 29, 2008

(65) Prior Publication Data

US 2008/0220079 A1 Sep. 11, 2008

Related U.S. Application Data

(60) Provisional application No. 60/904,456, filed on Mar. 2, 2007.

(51) Int. Cl.
| | |
|---|---|
| *A61K 9/16* | (2006.01) |
| *A61K 31/7008* | (2006.01) |
| *A61K 9/00* | (2006.01) |
| *A61K 31/522* | (2006.01) |
| *A61K 31/135* | (2006.01) |
| *A61P 3/02* | (2006.01) |

(52) U.S. Cl.
CPC .......... *A61K 9/1617* (2013.01); *A61K 9/1652* (2013.01); *A61K 9/1694* (2013.01); *A61K 31/135* (2013.01); *A61K 31/522* (2013.01); *A61K 31/7008* (2013.01); *A61K 9/0095* (2013.01)

(58) Field of Classification Search
None
See application file for complete search history.

(56) References Cited

U.S. PATENT DOCUMENTS

| | | | | |
|---|---|---|---|---|
| 3,908,028 | A | * | 9/1975 | Neely et al. ................ 426/538 |
| 4,761,450 | A | * | 8/1988 | Lakshmanan et al. ....... 524/488 |
| 5,188,841 | A | | 2/1993 | Simpkin et al. ............. 424/495 |
| 5,580,578 | A | | 12/1996 | Oshlack et al. |
| 5,582,351 | A | * | 12/1996 | Tsau .............................. 241/17 |
| 5,725,886 | A | | 3/1998 | Erkoboni et al. ............ 424/499 |
| 5,807,583 | A | * | 9/1998 | Kristensen et al. .......... 424/489 |
| 6,254,887 | B1 | | 7/2001 | Miller et al. |

(Continued)

FOREIGN PATENT DOCUMENTS

| | | |
|---|---|---|
| EP | 1527775 A1 | 5/2005 |
| FR | 2742659 | 6/1997 |

(Continued)

OTHER PUBLICATIONS

Horkovics-Kovats. Chemotherapy; Nov. 2004; 50, 5; Research Library. p. 234.*

(Continued)

*Primary Examiner* — Nicole P Babson
*Assistant Examiner* — Lori K Mattison
(74) *Attorney, Agent, or Firm* — Kilpatrick Townsend & Stockton LLP

(57) ABSTRACT

Sustained release spherical or non-spherical pellets comprising (a) an active ingredient (b) a wax-like agent, and (c) a spheronizing agent are provided. Oral dosage forms comprising the pellets and methods for preparing and using such pellets and dosage forms are also provided.

19 Claims, 8 Drawing Sheets

(56) References Cited

U.S. PATENT DOCUMENTS

| | | | |
|---|---|---|---|
| 6,290,990 B1* | 9/2001 | Grabowski | A61K 9/1617 424/499 |
| 6,436,438 B1 | 8/2002 | Momberger et al. | 424/458 |
| 6,620,611 B2* | 9/2003 | Hince | 435/262.5 |
| 6,673,367 B1* | 1/2004 | Goldenheim et al. | 424/464 |
| 6,699,506 B1 | 3/2004 | Paillard et al. | 424/489 |
| 6,897,205 B2 | 5/2005 | Beckert et al. | 514/159 |
| 6,984,403 B2 | 1/2006 | Hagen et al. | 424/489 |
| 7,074,430 B2 | 7/2006 | Miller et al. | |
| 2002/0045668 A1* | 4/2002 | Dang et al. | 514/649 |
| 2002/0086070 A1* | 7/2002 | Kuhrts | 424/773 |
| 2002/0151682 A1* | 10/2002 | Athwal et al. | 530/350 |
| 2003/0180352 A1* | 9/2003 | Patel | A61K 9/5078 424/465 |
| 2004/0208936 A1* | 10/2004 | Chorin et al. | 424/490 |
| 2004/0258749 A1* | 12/2004 | Guldner et al. | 424/464 |
| 2006/0068021 A1 | 3/2006 | Kuhrts | 424/490 |
| 2006/0153908 A1 | 7/2006 | Strong et al. | 424/451 |
| 2006/0193914 A1* | 8/2006 | Ashworth et al. | 424/469 |

FOREIGN PATENT DOCUMENTS

| | | |
|---|---|---|
| GB | 2 209 669 A | 5/1989 |
| JP | 01-156913 | 6/1989 |
| JP | 2-193914 | 7/1990 |
| JP | 02-275817 | 11/1990 |
| JP | 07-188058 | 7/1995 |
| JP | 11-504634 | 11/1996 |
| JP | 2000-507613 | 5/1998 |
| JP | 2003-506400 | 2/2003 |
| JP | 2005-508939 | 4/2003 |
| JP | 2004-24686 | 1/2004 |
| SK | 283143 | 12/1994 |
| WO | WO 92/12633 A1 | 8/1992 |
| WO | WO 96/01057 A1 | 1/1996 |
| WO | WO 98/42311 A1 | 10/1998 |
| WO | WO 00/35450 A1 | 6/2000 |
| WO | 01/10419 A1 | 2/2001 |
| WO | WO 01/58447 A1 | 8/2001 |
| WO | WO 03/020243 A1 | 3/2003 |
| WO | WO 2005/000310 A1 | 1/2005 |
| WO | WO 2005013953 * | 2/2005 ........... A61K 31/137 |

OTHER PUBLICATIONS

Microcrystalline Cellulose. http://www.pharma-excipients.com/micro-crystalline-cellulose.html. Archived Sep. 30, 2005. Accessed Aug. 30, 2005.*

Calcium Hydrogen Phosphate. http://www.icl-perfproductslp.com/mm/files/Dicalcium_Phosphate_Dihydrate_EN.pdf. Nov. 1, 2005.*

Funck..Drug Development and Industrial Pharmacy. 1991, vol. 17, No. 9. Abstract.*

Parikh. Handbook of Pharmaceutical Granulation Technology. Copyright 1997.*

Glucosamine. http://www.vitastock.com/articles/glucosamine.shtml. Archived Feb. 1, 2001. Accessed Aug. 14, 2010.*

Natural Treatments. http://www.allvita.net/glucosam.htm. Posted on Jan. 31, 2001. Accessed Aug. 14, 2010.*

Pellet. Merriam Webster Online Dictionary. Accessed Aug. 14, 2010.*

Vaughan, vol. 65, No. 4; p. 601-603. (Year: 1976).*

Tho, Ingunn, et al., "Extrusion/Spheronization of Pectin-Based Formulations. II. Effect of Additive Concentration in the Granulation Liquid," *AAPS PharmSciTech* 2(4):1-10, Dec. 3, 2001.

Waldron, Mike, "A practical guide to the extrusion and spheronization of pharmaceuticals using NICA™ System," *TechPapers/NICA*, pp. 1-26, Feb. 9, 2001—GB.

Biswal et al.; Production variables affecting characteristics of pellets in melt pelletization with wax combination in a laboratory scale spheronizer; Acta Pharm. 59 (2009) 199-210.

Gandhi, et al.; Using Extrusion-Spheronization to Develop Controlled-Release Formulations of Azithromycin; Pharmaceutical Technology (Feb. 2005) 68-86.

* cited by examiner

SUSTAINED RELEASE COMPOSITIONS USING WAX-LIKE MATERIALS

CROSS-REFERENCE TO RELATED APPLICATION

This application claims the benefit under 35 U.S.C. § 119(e) of U.S. Provisional Patent Application No. 60/904,456 filed Mar. 2, 2007, where this provisional application is incorporated herein by reference in its entirety.

BACKGROUND OF THE INVENTION

1. Field of the Invention

This invention relates to sustained release compositions and dosage forms and to methods of preparing and using such compositions and dosage forms.

2. Description of the Related Art

Oral pharmaceutical dosage forms usually come in single dosage unit forms, such as tablets or capsules. Each tablet or capsule unit contains a fixed amount of an active ingredient.

Many active ingredients require specific release kinetics or prolonged release. In such instances, use is made of so-called sustained or controlled release formulations. The term "sustained release" is often also used for formulations that show controlled release during a prolonged period of time. Controlled release formulations have been introduced for active ingredients that require a specific release pattern such as a constant release during a certain period of time, i.e., a release of an active ingredient that minimizes peaks and drops. Various controlled release formulations are now available that avoid temporary over- or under-dosing of the active ingredient. Sustained release formulations have been developed in which the release of the active ingredient is prolonged in some way in order to maintain therapeutic activity for a longer period of time. The terms of "sustained release" and "controlled release" are often interchangeable.

Sustained release formulations typically are applied to drugs that have a short half-life or for active ingredients that require active blood plasma levels for long periods of time. In the former instance, multiple daily dosing can be avoided such as b.i.d., t.i.d. or q.i.d regimens, which often lead to problems caused by lack of patient compliance. Sustained release formulations are more preferably applied for patients on chronic medication where one administration suffices to maintain active blood plasma levels for longer periods such as several days or even weeks.

Tablet and capsule dosage forms are convenient to use but suffer from limitations in delivering a drug that (1) requires a very high dose for its therapeutic benefits, (2) are for patients that do not take tablet/capsule voluntarily, or (3) are for those with swallowing difficulties.

For instance, one tablet that contains up to 0.75-1 gram of an active ingredient along with other inactive ingredients required for forming the tablets often ends up with rather bulky mass with a total weight up to 1.5-2 grams. Any further increase in active dose (e.g., more than 1 g) would render the tablet too big to swallow. Size of a capsule containing the same weight can be even greater because the capsule content is usually not compressed like a tablet.

A sustained release oral dosage form is intended to deliver a drug in one unit for a prolonged therapeutic duration such as ½, 1, 2, or even 3 days. A sustained release formulation is often not feasible as a tablet or capsule due to their unacceptably large size. For example, for a drug that is administered 3 times a day at 500 mg each time in a non-sustained release formulation, a once-a-day dose (i.e., 1500 mg) would result in a bulky tablet with a total weight of greater than 2-3 grams. Such a bulky tablet would be very difficult to swallow by a human or animal subject.

It is difficult to give tablets or capsules to animals such as horses, cats or dogs because they do not take tablets or capsules voluntarily, and poking down a tablet or capsule can be very cumbersome. Similarly, some human patients do not like to or unable to swallow tablets or capsules, especially the large ones.

Multiparticulate formulations are of particular use in overcoming the aforementioned shortcomings associated with tablet or capsule formulations.

Multiparticulates are well-known dosage forms that comprise a multiplicity of drug-containing particles whose totality represents the intended therapeutically useful dose of a drug. A multiparticulate dosage form can be made with a pure drug substance or formulated with other ingredients with typical particle size of 1-2 mm or less. When taken orally, multiparticulates generally disperse freely in the gastrointestinal tract, exit relatively rapidly and reproducibly from the stomach, and maximize absorption. See, for example, Multiparticulate Oral Drug Delivery (Marcel Dekker, 1994) and Pharmaceutical Pelletization Technology (Marcel Dekker, 1989).

A multiparticulate formulation may be represented by other terms such as powders, granules, pellets, microspheres, minispheres, beadlets, sachets etc. Because for each dose, multiple units of particles are given, the term multi-unit dosage form is used.

A multiparticulate formulation may be dosed as (1) dry powder which is placed in mouth and swallowed with liquid, (2) dispersed in a liquid and then swallowed, or (3) placed in a capsule. For the $1^{st}$ and $2^{nd}$ methods of administration, large amounts of particles can be given. For example, 5-10 grams of spherical pellets can be suspended in water and swallowed easily by a human patient. For animals such as horse, a multiparticulate formulation can be readily mixed with feed and be consumed by the animal voluntarily. Moreover, unlike humans, animals are usually dosed based on body weight. Animals have a tremendous variability in body weights. For example, dogs may have body weights ranging from 2 kg to 50 kg, requiring the dosage form be administered in very specific quantities adjusted according to body weight of the patient. In such instances, a multiparticulate formulation is of particular use because its dose can be adjusted easily by weighing or measuring by volume or counting the number of pellets to give a wide range of dose variation, e.g., from about 10 mg (1 pellet) to 100 g (10,000 pellets).

Numerous active ingredients require sustained release kinetics or prolonged release such as twice-a-day, preferably once-a-day, or ever more preferable once every 2-3 days. In such instances, use is made of so-called sustained release multiparticulate formulations. Because of the allowance for a high dosing volume, a sustained release multiparticulate formulation is particularly useful for drugs that are given at a high dose, e.g., more than 1000 mg per dose.

Unlike the tablets where a sustained release may be obtained by a matrix and/or coating system, known sustained release multiparticulate formulations rely almost exclusively on a coating system to provide a barrier to the drug release, i.e., "sustained release coating." This is due to the greatly increased surface area of a small pellet of 1-2 mm diameter compared to a tablet. For example, a tablet in disc shape of 10 mm diameter and 5 mm thickness contains the same volume as 750 spheres of 1 mm diameter. Given the same density, the 750 spheres combined have 30 times of the surface area of the tablet of the same weight. According to the Noyes-Whitney equation which was developed by Noyes and Whitney in 1897:

$$-dM/dt = KA(Cs-C)$$

where −dM/dt is the drug dissolution rate of a drug from a matrix, K is the diffusion constant, A is the surface area and (Cs−C) is the concentration differential between the unstirred surface layer adjacent to solid mass and bulk of the dissolution medium.

It is clear that the dissolution rate of a drug is directly proportional to the surface of the matrix mass, i.e., a matrix tablet or spheres. The overall drug dissolution rate of 750 spheres of 1 mm diameter is thus 30 times faster than a tablet of the same volume and density. In other words, a matrix tablet capable of releasing its drug in 24 hours would release the drug in about 0.8 hour should it be converted to spheres of 1 mm diameter of the same matrix mass. This dramatic increase in surface area and thus dissolution rate has made sustained release spheres almost impossible without a barrier coating, because most matrix-forming materials and the conventional matrix manufacturing processes are incapable of providing sufficiently prolonged drug dissolution. A barrier coating is required for almost all known sustained release pellets (see, U.S. Patent Application Publication No. 2006/0153908, U.S. Pat. Nos. 5,188,841, 6,699,506, 6,897, 205, and 6,436,438).

BRIEF SUMMARY OF THE INVENTION

The present invention provides pharmaceutical compositions for sustained release of pharmaceutically active agents and methods for preparing and using such pharmaceutical compositions. The pharmaceutical compositions are in the form of pellets and may have one or more of the following characteristics: (1) providing sustained release that does not require a sustained release barrier coating, which lowers the cost associated with the barrier coating and decreases scale-up complexity; (2) providing the flexibility for dosing, especially for animal patients; (3) enabling slow release of active ingredients due to relatively large sizes of the pellets (e.g., at least about 0.5 mm or 1 mm in diameter for spherical pellets), which enables slow release of active ingredients; and (4) easier to administer pharmaceutically active agents of short half-lives and/or high doses compared to tablets or capsules.

In one aspect, the present invention provides a composition that comprises (a) an active ingredient, a wax-like agent, and a spheronizing agent, (b) is in the form of pellets, and (c) provides sustained release of the active ingredient. In certain embodiments, the composition provides such sustained release without the need for a sustained release barrier coating.

In certain embodiments, the pellets are uncoated. In certain other embodiments, the pellets are coated. The coating may be a sustained release barrier coating, a taste masking barrier, a moisture barrier, a color barrier, or an enteric-coating.

In certain embodiments, the pellets are spherical. In other embodiments, the pellets are non-spherical.

In certain embodiments, the composition has an in vitro dissolution rate measured by standard USP basket method according to Example 3 of at most about 50%, 60%, 70%, 80%, or 90% of the active ingredient released after 2 hours.

In certain embodiments, the composition has an in vitro dissolution rate measured by standard USP basket method according to Example 3 of: about 10% to about 60% of the active ingredient released after 1 hour; about 20% to about 70% of the active ingredient released after 2 hours; about 30% to about 80% of the active ingredient released after 4 hours; and about 40% to about 90% of the active ingredient release after 8 hours; and about 50% to about 100% of the active ingredient release after 12 hours. In certain embodiments, the active ingredient is glucosamine or a pharmaceutically acceptable salt thereof.

In certain embodiments, the composition has an in vitro dissolution rate measured by standard USP basket method according to Example 3 of: about 0% to about 30% after 2 hours; about 5% to about 35% after 4 hours, about 10% to about 40% after 8 hours; about 15% to about 45% after 16 hours; about 20% to about 50% after 24 hours. In certain embodiments, the active ingredient is tramadol or a pharmaceutically acceptable salt thereof.

In certain embodiments, upon or after oral administration, the composition provides a 2-phase release profile, where the first phase releases 10-60% of the active ingredient in about 1 hour and the second phase releases the rest of the active ingredient, in a nearly linear fashion, for at least about 2, 3, 4, 5, 6, 7, 8, 9, 10, 11, 12, 14, 16, 18, 20, 22, or 24 hours.

In certain embodiments, the composition comprises: (a) from about 5% to about 90% of the active ingredient; (b) from about 5% to about 40% of the wax-like agent; and (c) from about 5% to about 40% of the spheronizing agent.

In certain embodiments, the composition may further comprise one or more inactive ingredients. In certain embodiments, the inactive ingredients may be binders, antioxidants or colorants. In certain embodiments, the inactive ingredient(s) may be present at a total concentration from about 0.01% to about 5.0% based on the pellet weight.

In certain embodiments, the active agent may be an analgesic or a pharmaceutically acceptable salt thereof, such as acetaminophen, a centrally acting analgesic agent, opiate, narcotic, nonsteroidal anti-inflammatory drugs (NSAIDS), and salicylate. In certain embodiments, the analgesic is tramadol or a pharmaceutically acceptable salt thereof.

In certain embodiments, the composition comprises: (a) from about 45% to about 85% of an analgesic or a pharmaceutically acceptable salt thereof; (b) from about 5% to about 30% of hydrogenated vegetable oil (e.g., cottonseed oil); (c) from about 5% to about 20% of microcrystalline cellulose; and (d) from about 1% to about 10% pregelatinized starch.

In certain embodiments, the active ingredient is a dietary supplement, such as vitamins, minerals, herbs or other botanicals, amino acids, proteins, and other nutrient substances or their constituents. In certain embodiments, the dietary supplement is glucosamine or a pharmaceutically acceptable salt thereof.

In certain embodiments, the composition comprises: (a) from about 45% to about 85% of a dietary supplement or a pharmaceutically acceptable salt thereof; (b) from about 5% to about 30% of hydrogenated vegetable oil (e.g., cottonseed oil); (c) from about 5% to about 20% of microcrystalline cellulose; and (d) from about 1% to about 10% pregelatinized starch.

In certain embodiments, the active ingredient is an antiviral agent or a pharmaceutically acceptable salt thereof, such as abacavir, acyclovir, ganciclovir, lammivudine, nelfinavir, ritonavir, valacyclovir, foscarnet, and zidovudine, or a derivative, prodrug or pharmaceutically acceptable salt thereof.

In certain embodiments, the composition comprises: (a) from about 45% to about 85% of an antiviral agent or a pharmaceutically acceptable salt thereof; (b) from about 5% to about 30% of hydrogenated vegetable oil (e.g., cottonseed oil); (c) from about 5% to about 30% of microcrystalline cellulose; and (d) from about 1% to about 10% pregelatinized starch.

In certain embodiments, the active ingredient is an anti-infective agent or a pharmaceutically acceptable salt thereof, such as antibiotics (including β-lactam antibiotics, aminoglycosides, cephalosporins, macrolides, penicillins, quinolones, sulfonamides, tetracyclines, antifungals, antimalarial agents, antituberculosis agents, and anti-parasitics). In certain embodiments, the anti-infective agent is azithromycin, clarithromycin, roxithromycin, erythromycin, ciprofloxacin, a combination of amoxicillin and clavulanate potassium, or a derivative, prodrug, a pharmaceutically acceptable salt thereof.

In certain embodiments, the composition comprises: (a) from about 45% to about 85% of an anti-infective agent or a pharmaceutically acceptable salt thereof, (b) from about 5% to about 30% of hydrogenated vegetable oil (e.g., cottonseed oil), (c) from about 5% to about 30% of microcrystalline cellulose, and (d) from about 1% to about 10% pregelatinized starch.

In certain embodiments, the active ingredient is an antacid, such as sodium antacid, calcium antacids, aluminum antacids, magnesium antacids, and combinations thereof. In certain embodiments, the antacid is aluminum hydroxide, magnesium hydroxide, trisodium phosphate (also referred to as "sodium phosphate tribase") or a combination of two or all of these three compounds. In certain embodiments, the antacid is a combination of aluminum hydroxide and magnesium hydroxide, or a combination of trisodium phosphate and magnesium hydroxide, at a weight ratio of about 1:3, 1:2, 1:1, 2:1, or 3:1.

In certain embodiments, the composition comprises: (a) from about 45% to about 85% of an antacid, (b) from about 1% to about 30% of hydrogenated vegetable oil (e.g., cottonseed oil), (c) from about 5% to about 30% of microcrystalline cellulose, and (d) from about 1% to about 10% pregelatinized starch.

In certain embodiments, the active ingredient is a high-dose drug, such as fenbendazole, albendazole, febantel, carprofen, ketoprofen, diclofenac, morphine, meperidine, buprenorphine, butorphanol, metronidazole, potassium bromide, gabapentin, zileuton, sucralfate, metformin, glipizide, nabumetone, niacin, procainamide, tolmetin sodium, choline magnesium trisalicylate, guaifenesin, eprosartan mesylate, etodolac, acarbose, ursodiol, polyene phosphatidylcholine, and a pharmaceutically acceptable salt thereof.

In certain embodiments, the composition comprises: (a) from about 45% to about 90% of a high-dose pharmaceutically active agent, (b) from about 5% to about 40% of hydrogenated vegetable oil (e.g., cottonseed oil), (c) from about 5% to about 40% of microcrystalline cellulose, and (d) from about 1% to about 10% pregelatinized starch.

In certain embodiments, the active ingredient is an insect growth regulator (IGR) or a pharmaceutically acceptable salt thereof, such as methoprene, kinoprene, hydroprene, diflubenzuron, or pyriproxifen.

In certain embodiments, the composition comprises: (a) from about 45% to about 85% of an insect growth regulator or a pharmaceutically acceptable salt thereof; (b) from about 5% to about 30% of hydrogenated vegetable oil (e.g., cottonseed oil); (c) from about 5% to about 30% of microcrystalline cellulose; and (d) from about 1% to about 10% pregelatinized starch.

In certain embodiments, the pellets are coated. The coating may or may not contribute to sustained release of the composition.

In certain embodiments where the pellets are spherical, their average diameter is about 0.1 mm to about 3 mm, about 0.5 mm to about 2 mm, or 0.5 mm to about 1.5 mm.

In certain embodiments, the wax-like agent is selected from the group consisting of fatty alcohols, saturated and unsaturated fatty acid esters, saturated and unsaturated fatty acid glycerides, hydrogenated fats, hydrogenated vegetable oil, and cholesterol. In certain embodiments, the wax-like agent is hydrogenated vegetable oil.

In certain embodiments, the wax-like sustained release agent has a melting point at least about 40° C., 50° C., or 60° C.

In certain embodiments, the spheronizing agent is microcrystalline cellulose.

In another aspect, the present invention provides a dosage form that comprises the composition described herein.

In certain embodiments, the dosage form comprises the active ingredient at a dose of at least about 1, 2, 3, 4, 5, 6, 7, 8, 9, or 10 g per dose.

In certain embodiments, the dosage form further comprises one or more inactive ingredients, such as flavorants, suspending agents, anticaking agents, fillers, sweeteners, colorants, and lubricants.

In certain embodiments, the dosage form further comprises water and is in the form of an oral suspension.

In certain embodiments, the dosage form may be packaged in a bottle, packet, pouch, sachet, or capsule.

In certain embodiments, the dosage form, upon oral administration to a patient in need thereof, provides a plasma concentration of the active agent at or above its minimum effective concentration for at least about 2, 4, 6, 8, 10, 12, 14, 16, 18, 20, 24, 36, 48, 72, 96, 120, 144, or 168 hours.

In certain embodiments, the dosage form, upon oral administration to a patient in need thereof, provides a plasma concentration of the active agent at or above its minimum effective concentration for a period of time that is at least about 2, 3, 4, or 5 times of that of an immediate release formulation administered at a standard dose.

In certain embodiments, the dosage form is suitable for administration to a patient in need thereof at or no more than once or twice per day, once per two, three, four, five, six, seven days, once per one, two, three, or four weeks, or once per treatment.

In another aspect, the present application provides a method for making spherical or non-spherical pellets comprising (i) an active ingredient; (ii) a wax-like agent; and (iii) a spheronizing agent, the method comprising: (a) preparing a mixture of the active ingredient, the wax-like agent, the spheronizing agent, and a liquid; (b) extruding said mixture to obtain an extrudate; (c) spheronizing the extrudate to form spherical pellets or fragmenting the extrudate to form non-spherical pellets; (d) drying the spherical pellets; and (e) heating the dry pellets to a temperature higher than the melting point of the wax-like agent.

For example, in certain embodiments, the present application provides a method for making spherical pellets comprising (i) an active ingredient; (ii) a wax-like agent; and (iii) a spheronizing agent, the method comprising: (a) preparing a mixture of the active ingredient, the wax-like agent, the spheronizing agent, and a liquid; (b) extruding said mixture to obtain an extrudate; (c) spheronizing the extrudate to form spherical pellets; (d) drying the spherical pellets; and (e) heating the dry pellets to a temperature higher than the melting point of the wax-like agent.

In certain related embodiments, the present invention provides a method for making spherical pellets comprising above steps (a) to (d), but not above step (e).

In certain embodiments, the spherical pellets are subsequently mixed with a flavorant or a vehicle comprising one or more inactive ingredients, such as flavorants.

In certain embodiments, the liquid is water. In certain other embodiments, the liquid comprises water and an organic solvent (e.g., propylene glycol, ethanol, or isopropanol).

In certain other embodiments, the present application provides a method for making non-spherical pellets comprising (i) an active ingredient; (ii) a wax-like agent; and (iii) a spheronizing agent, the method comprising: (a) preparing a mixture of the active ingredient, the wax-like agent, the spheronizing agent, and a liquid; (b) extruding said mixture to obtain an extrudate; (c) fragmenting the extrudate to form non-spherical pellets; (d) drying the non-spherical pellets; and (e) heating the dry pellets to a temperature higher than the melting point of the wax-like agent.

In a related aspect, the present invention provides a method for making non-spherical pellets comprising above steps (a) to (d), but not above step (e).

In certain embodiments, the non-spherical pellets are subsequently mixed with a vehicle comprising one or more inactive ingredients, such as flavorants.

In certain embodiments, the liquid is water. In certain other embodiments, the liquid comprises water and an organic solvent (e.g., propylene glycol, ethanol, or isopropanol).

In another aspect, the present invention also provides spherical and non-spherical pellets produced according to the methods described herein.

In another aspect, the present invention further provides methods for making dosage forms that comprise the compositions disclosed herein.

In certain embodiments, the method for making a dosage form comprises filling the pellets disclosed herein in a suitable container, such as capsules, bottles, and pouches.

In certain embodiments, the method for making a dosage form comprises mixing the pellets disclosed herein with a vehicle, and suspending the resulting mixture in water or another solution to form oral suspension dosage form.

In certain embodiments, the method for making a dosage form comprises mixing the pellets with human food or animal feed.

In another aspect, the present invention provides a method of treating an animal in need thereof, comprising administering to the animal orally a composition or a dosage form containing an effective amount of the composition described herein.

For example, in one aspect, the present invention provides a method for reducing pain, comprising administering orally to a patient in need thereof a composition described herein that comprises an effective amount of an analgesic or a pharmaceutically acceptable salt thereof.

In another aspect, the present invention provides a method for treating or preventing dietary deficiency, comprising administering orally to a patient in need thereof a composition described herein that comprises an effective amount of a dietary supplement or a pharmaceutically acceptable salt thereof.

In another aspect, the present invention provides a method for treating or preventing viral infection, comprising administering orally to a patient in need thereof a composition described herein that comprises an effective amount of an anti-viral agent or a pharmaceutically acceptable salt thereof.

In another aspect, the present invention provides a method for treating or preventing bacterial infection, comprising administering orally to a patient in need thereof a composition described herein that comprises an effective amount of an anti-infective agent or a pharmaceutically acceptable salt thereof.

In another aspect, the present invention provides a method for treating or preventing gastrointestinal ulcer or disorder, comprising administering orally to a patient in need thereof a composition described herein that comprises an effective amount of an antacid or a pharmaceutically acceptable salt thereof.

In certain embodiments, the method for treating or preventing gastrointestinal ulcer or disorder comprises administering orally to a patient in need thereof a mixture of a composition that comprises aluminum hydroxide and magnesium hydroxide described herein and a composition that comprises sodium phosphate tribase described herein. In certain embodiments, the ratio of the total weight of aluminum hydroxide and magnesium hydroxide to sodium phosphate tribase is about 9:1.

In certain embodiments, the present invention provides a method for treating or preventing parasite or pest infestation that comprises administering orally to a patient in need thereof a composition described herein that comprises an effective amount of an insect growth regulator.

DETAILED DESCRIPTION OF THE INVENTION

Figure 1:
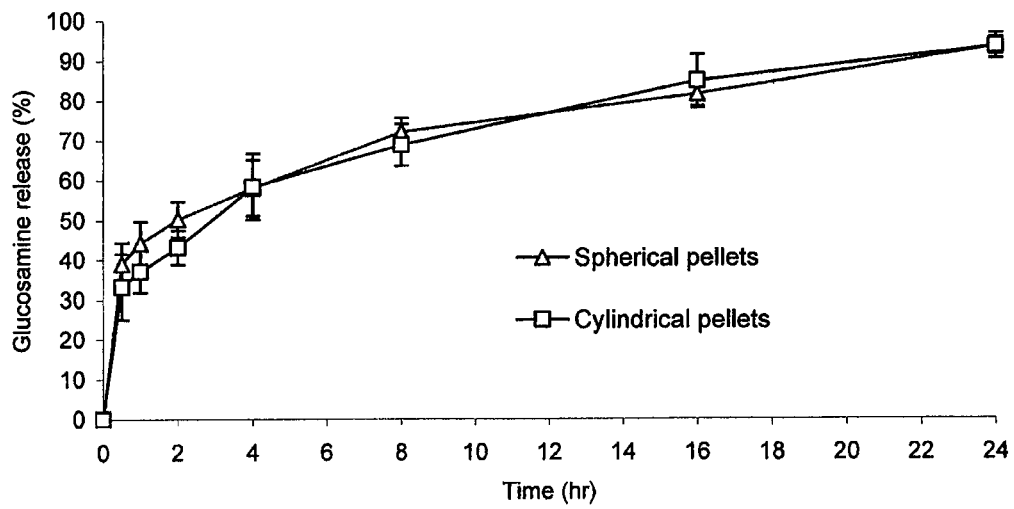
FIG. 1. Representative dissolution profiles from spherical and non-spherical pellets prepared according to Examples 1 and 2.

The present invention provides pharmaceutical compositions for sustained release of pharmaceutically active agents in the form of pellets, which do not require the presence of a sustained release barrier coating. In addition, the present invention provides dosage forms that comprise such compositions. It further provides methods for preparing and using the pharmaceutical compositions and dosage forms.

Unless indicated otherwise, any percentage is weight by weight (w/w) relative to the total weight of a composition or to the total weight of a dry pellet.

As used in the present invention, the term "about" refers to any value in the range of 90% to 110% of a specified value. For example, about 40° C. refers to any temperature from 36° C. to 44° C.

As used in the present invention, any numerical ranges recited herein are to be understood to include any integer within the range and, where applicable (e.g., concentrations), fractions thereof, such as one tenth and one hundredth of an integer (unless otherwise indicated).

I. Compositions

In one aspect, the present invention provides a composition that (a) comprises (i) an active ingredient, (ii) a wax-like agent, and (iii) a spheronizing agent, (b) is in the form of pellets, and (c) provides sustained release of the active ingredient. In certain embodiments, the sustained release of the active ingredient does not require the presence of a sustained release barrier coating on the pellets.

A. Active Ingredient

The active ingredient in the composition may be any pharmaceutically active agent (i.e., a compound or a composition, such as a herb extract, with beneficial pharmaceutical, therapeutic, nutritional, or cosmetic effects).

In certain embodiments, the active agent may be an analgesic or a pharmaceutically acceptable salt thereof, such as acetaminophen, a centrally acting analgesic agent, opiate, narcotic, nonsteroidal anti-inflammatory drugs (NSAIDS), and salicylate. In certain embodiments, the active agent is a combination of two or more analgesics or their pharmaceutically acceptable salts thereof. In certain embodiments, the analgesic is tramadol or a pharmaceutically acceptable salt thereof (e.g., tramadol HCl).

In certain embodiments, the active ingredient is a dietary supplement, such as vitamins, minerals, herbs or other botanicals, amino acids, proteins, and other nutrient substances or their constituents. In certain embodiments, the active agent is a combination of two or more dietary supplements. In certain embodiments, the dietary supplement is glucosamine or a pharmaceutically acceptable salt thereof.

In certain embodiments, the active ingredient is an antiviral agent or a pharmaceutically acceptable salt thereof, such as abacavir, acyclovir, ganciclovir, lammivudine, nelfinavir, ritonavir, valacyclovir, and zidovudine. In certain embodiments, the active agent is a combination of two more antiviral agents or their pharmaceutically acceptable salts.

In certain embodiments, the active ingredient is an anti-infective agent or a pharmaceutically acceptable salt thereof, such as antibiotics (including β-lactam antibiotics, aminoglycosides, cephalosporins, macrolides, ketolides, penicillins, quinolones, sulfonamides, tetracyclines, cycloserine, vancomycin, linezolid, oxazolidinone, pyrimethamine, atovaquone, tigecycline, glycylcyclines, anthelmintics, antifungals, antimalarial agents, antiprotozoal agents, leprostatics, antituberculosis agents, and anti-parasitics. In certain embodiments, the anti-infective agent is azithromycin, clarithromycin, roxithromycin, erythromycin, telithromycin, ciprofloxacin, a combination of amoxicillin and clavulanate potassium, or a pharmaceutically acceptable salt thereof. In certain embodiments, the active agent is a combination of two or more anti-infective agents or their pharmaceutically acceptable salts.

In certain embodiments, the active ingredient is an antacid, such as sodium antacids (e.g. trisodium phosphate, also referred to as "sodium phosphate tribase"), calcium antacids (e.g. calcium carbonate), aluminum antacids (e.g., aluminum hydroxide), magnesium antacids (e.g., magnesium hydroxide), and combinations thereof. In certain embodiments, the antacid is aluminum hydroxide, magnesium hydroxide, trisodium phosphate (also referred to as "sodium phosphate tribase") or a combination of two or all of these three compounds. In certain embodiments, the antacid is a combination of aluminum hydroxide and magnesium hydroxide, or a combination of trisodium phosphate and magnesium hydroxide at a weight ratio of about 1:3, 1:2, 1:1, 2:1, or 3:1.

In certain embodiments, the active ingredient is an insect growth regulator (IGR) or a pharmaceutically acceptable salt thereof, such as methoprene, kinoprene, hydroprene, diflubenzuron, or pyriproxifen. In certain embodiments, the active ingredient is a combination of two or more insect growth regulators or their pharmaceutically acceptable salts.

In certain embodiments, the composition comprises: (a) from about 45% to about 85% of an insect growth regulator or a pharmaceutically acceptable salt thereof; (b) from about 5% to about 30% of hydrogenated cottonseed oil; (c) from about 5% to about 30% of microcrystalline cellulose; and (d) from about 1% to about 10% pregelatinized starch.

In certain embodiments, the active ingredient is a high dose pharmaceutically active agent. A pharmaceutically active agent of "high dose" refers to a pharmaceutically active agent that is orally administered at a daily dose of about or greater than 1 mg/kg body weight to an adult human patient or an adult non-human subject (e.g., a dog, cat, horse, pig, etc.). In certain embodiments, the pharmaceutically active agent of the present invention has a daily dose about or greater than 2, 3, 4, 5, 6, 7, 8, 9, 10, 20, 30, 40, or 50 mg/kg body weight for an adult human or an adult non-human subject. In certain embodiments, the pharmaceutically active agent of the present invention has a daily dose about or greater than 100, 200, 250, 300, 350, 400, 450, 500, 600, 700, 800, 900, or 1000 mg for an adult human or an adult non-human subject. In certain embodiments, the active ingredients are those that must be given at least about 200 mg, 300 mg, 400 mg, 500 mg, 600 mg, 700 mg, 800 mg, 900 mg, or 1 g per dose in a twice-a-day, once-a-day or once-per-treatment regimen.

Exemplary pharmaceutically active agents of high dose include tramadol (e.g., tramadol HCl) (100 mg/dose or more), acyclovir (200 mg/dose), acetaminophen (300 mg/dose), metformin (e.g., metformin HCl) (500 mg/dose), gabapentin (100-800 mg/dose), glucosamine, glucosamine sulfate, glucosamine HCl (500 mg/dose), etc.

Additional examples of the high-dose ingredients are niacin, azithromycin, valacyclovir, ursodiol, polyene phospholipids, cholestyramine, chitosan, fenbendazole, albendazole, febantel, carprofen, ketoprofen, diclofenac, morphine, meperidine, buprenorphine, butorphanol, metronidazole, potassium salts, zileuton, sucralfate, glipizide, nabumetone, procainamide, tolmetin sodium, choline magnesium trisalicylate, guaifenesin, eprosartan mesylate, etodolac, acarbose, ursodiol, polyene phosphatidylcholine, a pharmaceutically acceptable salt thereof, vitamins, minerals, irons, antacids, herbal extracts, and the like.

In certain embodiments, the active ingredient is a combination of two or more high dose pharmaceutically active agents or their pharmaceutically acceptable salts. The two or more high dose pharmaceutically active agents may or may not have similar pharmaceutical effects.

A "pharmaceutically acceptable salt" of a pharmaceutically active agent refers to a salt (including an acid addition salt) of the pharmaceutically active agent, within the scope of sound medical judgment, suitable for use in contact with the tissues of humans and lower animals without undue toxicity, irritation, allergic response, and the like, and effective for the intended use of the pharmaceutically active agent.

In certain embodiments, the active ingredient is therapeutically effective for a human (e.g., an adult human patient) or non-human subject (e.g., a dog, a cat, a horse, a pig, etc.) at a daily dose of at least about 5 mg/kg of the body weight of the subject, such as at least about 7.5, 10, 12, 14, 16, 18, 20, 25, 30, 35, 40, or 50 mg/kg of the body weight of the subject.

In certain embodiments, the active ingredient has a short half-life. A pharmaceutically active agent of "short half-life" refers to a pharmaceutically active agent that has a half-life about or less than 10 hours. In certain embodiments, the pharmaceutically active agent of the present invention has a half-life of about or less than about 9, 8, 7, 6, 5, 4, 3, or 2 hours in a human (e.g., an adult human patient) or non-human subject (e.g., a dog, cat, horse, pig, etc.). In general, a pharmaceutically active agent of a short half-life is required to be taken more than twice a day in its immediate release forms to maintain the efficacious blood concentration level through the day.

In certain embodiments, the active ingredient is of both short half-life and high dose. Such active ingredients include, but not limited to: verapamil HCl, potassium chloride, cefdnir, propafenone HCl, hydroxyurea, hydrocodone bitartrate, delavirdine mesylate, nelfinavir meslyate, pentosan polysulfate sodium, tocainide HCl, quetiapine fumarate, fexofenadine HCl, carafate, rifampin, moxifloxacin HCl, praziquantel, ciprofloxacin, phosphate sodium potassium, methenamine mandelate, sotalol HCl, cefprozil, cefadroxil, metformin HCl, irbesartan, nefazodone HCl, gatifloxacin, didanosine, modafinil, efavirenz, metaxalone, amantadine HCl, morphine sulfate, mefenamic acid, diltiazem HCl, sevelamer HCl, albendazole, amoxicillin, clavulanate potassium, lithium carbonate, lamivudine, sumatriptan succinate, nabumetone, zidovudine, cimetidine, chlorpromazine HCl, valacyclovir HCl, bupropion HCl, ranitidine, abacavir sulfate, acyclovir, aminobenzoate potassium, pyridostigmine bromide, potassium chloride, isosorbide mononitrate, nicin, demeclocycline HCl, cefixime, naproxen sodium, tetratcycline HCl, cefuroxime axetil, propoxyphene napsylate, pyrazinamide, flecainide acetate, simethicone, mebendazole, methdopa, chlorathiazide, indinavir, penicillamine, meyyrosine, losartan potassium, thiobendazole, norfloxacin, hydroxyurea, procainamide, entacapone, valsartan, terbinafine HCl, metaprolol tartrate, ofloxacin, levofloxacin, chlorzoxazone, tolmetin sodium, tramadol HCl, bepridil HCl, phenytoin sodium, atorvastatin calcium, gabapentine, celecoxib, fluconazole, doxepine HCl, trovafloxacin mesylate, azithromycin, sertraline HCl, rifabutin, cefpodoxime proxetil, mesalamine, etidronate disodium, nitrofurantoin, choline magnesium trisalicylate, theophylline, nizatidine, pancreatin, quinidine sulfate, methocarbamol, mycophenolate mefetil, ganciclovir, saquinavir mesylate, tolcapne, ticlopidine HCl, valganciclovir HCl, capecitabine, orlistat, colsevelam HCl, irbesartan, succimer, meperidine HCl, hydroxychloroquine sulfate, guaifenesine, eprosartan mesylate, aminodarone HCl, felbamate, pseudoephedrine sulfate, carisoprodol, venlafaxine, propanolol HCl, etodolac, acebutolol, chondrotin, pyruvate, water soluble vitamins, creatine, Isoflavone, betaine HCl, psyllium, pantothenic Acid, zinc chloride, zinc gluconate, zinc sulfate, hytoestrogen, pycnogenol, proanthocyanidin, suntheanine, methylsulfonyl-methane, L-glutamine, colostrums, biotin, acetyl-L-carnitine, inositol, L-tyrosine, s-adenosyl methionine, bromelain, 2-dimethylaminoethanol, chromium picolinate, and combinations thereof.

In certain embodiments, the active ingredient may be insoluble, slightly soluble, sparingly soluble, soluble, freely soluble or very soluble in water. These terms are defined in the following table from Remington's Pharmaceutical Sciences, Mack Publishing Co., Easton, Pa., the latest edition.

| Descriptive terms | Parts of solvent needed for 1 part solute |
| --- | --- |
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Practically insoluble or insoluble | >10,000 |

In certain embodiments, the active ingredient is present in an amount of at least about 0.1%, 1%, 5%, 10%, 15%, 20%, 25%, 30%, 35%, 40%, 45%, or 50%, 55%, or 60% of the total weight of the composition. In certain embodiments, the active ingredient is present in an amount of at most about 65%, 70%, 75%, 80%, 85%, 90%, or 95% of the total weight of the composition. In certain embodiments, the active ingredient is present in the range of from about 0.1% to about 95%, such as from about 40% to about 85%, from about 50% to about 75%, from about 55% to about 70%, or from about 60% to about 65%, or any other range between any one of the above-noted minimum amount and any one of the above-noted maximum amount, w/w relative to the total weight of the composition.

In certain embodiments, the composition may further comprise a second pharmaceutically active agent. In certain embodiments, the second pharmaceutically active agent may be of high dose and/or short half-life. For example, in certain embodiments, the active ingredient may comprise glucosamine hydrochloride and chondroitin sulfate, tramadol hydrochloride and glucosamine hydrochloride, or tramadol hydrochloride and acetaminophen.

In certain embodiments, the other pharmaceutically active agent may have a same or similar pharmaceutical effect as the first pharmaceutically active agent in a pharmaceutical composition. For instance, a pharmaceutical composition of the present invention may comprise tramadol and another analgesic agent. In certain embodiments, the second pharmaceutically active agent may have a pharmaceutical effect different from the first pharmaceutically active agent. For instance, a pharmaceutical composition of the present invention may comprise glucosamine, chondroitin, manganese sulfate and calcium ascorbate.

In the embodiments where a pharmaceutical composition comprises two or more pharmaceutically active agents that produce an additive pharmaceutical effect, the amount of each agent is generally lower than that used for each agent in monotherapy (i.e., when the agents are given alone). For example, in one embodiment, the dose of each agent in the composition may be from 0.1 to 0.75 of the dose used in monotherapy, such as from 0.25 to 0.75 of the dose used in monotherapy. In another embodiment, the dose of one agent is one quarter of its normal dose used in monotherapy, and the dose of the other agent is three quarters of its normal dose used in monotherapy. In another embodiment, the dose of each agent is approximately one half of its normal dose when used in monotherapy.

In the embodiments where a pharmaceutical composition comprises two or more pharmaceutically active agents that produce a synergistic pharmaceutical effect, the combined dose of the agents is lower than that if the two agents produce only an additive pharmaceutical effect. For example, in one embodiment, the dose of one agent is one quarter of its normal dose used in monotherapy, and the dose of the other agent is also quarter of its normal dose used in monotherapy.

In the embodiments where a pharmaceutical composition comprises two or more agents that produce different pharmaceutical effects, the amount of each agent should be sufficient to produce the intended effect of the agent. In most of embodiments, the dose of each agent is similar to that used in monotherapy. In certain other embodiments, the dose of each agent may be higher or lower than that used in monotherapy.

The weight ratio of the first agent to the second agent in a pharmaceutical composition of the present invention depends on both agents and their dosages used in monotherapy. In certain embodiments, the weight ratio of the first agent to the second agent in a pharmaceutical composition is from about 1:1000 to 1000:1, such as 1:100 to 100:1, 1:50 to 50:1, 1:10 to 10:1, 1:5 to 5:1, 1:2 to 2:1, 1:1 to 1:10, 1:1 to 1:50, 1:1 to 1:100, 100:1 to 1:1, 50:1 to 1:1, or 10:1 to 1:1.

In certain embodiments, the pharmaceutical composition comprises tramadol and another analgesic agent. For example, in certain embodiments, the pharmaceutical composition comprises tramadol and an opioid analgesic. In certain other embodiments, the pharmaceutical composition comprises tramadol and a non-steroidal anti-inflammatory drug (NSAID).

Exemplary opioid analgesics that may be included in tramadol-containing pharmaceutical compositions include, but are not limited to, alfentanil, alphaprodine, anileridine, apomorphine, betaprodine, buprenorphine, butorphanol, carfentanil, codeine, codeinone, cyclorphan, cylcazocine, dextromethorphan, dextropropoxyphene, diamorphine (heroin), dihydrocodeine, diphenoxylate, ethoheptazine, etorphine, fentanyl, hydrocodone, hydromorphone, isomethadone, levallorphan, levorphanol, loperamide, meperidine, methadone, metopon, morphine, morphinone, nalbuphine, normorphine, N-(2-phenylethyl)-normorphine, oxycodone, oxymorphone, pentazocine, pethidine (meperidine), phenazocine, piminodine, propoxyphene, racemorphan, remifentanil, and sufentanil.

Exemplary NSAIDs that may be included in tramadol-containing pharmaceutical compositions include, but are not limited to, aspirin, carprofen, deracoxib, etodolac, firocoxib, celecoxib, diclofenac, diflunisal, fluriprofen, ibuprofen, indomethacin, ketoprofen, kietorolac, mefenamic acid, meloxicam, naproxen, phenylbutazone, piroxicam, rofecoxib, sulindac, and valdecoxib.

In certain embodiments, the pharmaceutical compositions of the present invention comprise both tramadol and acetaminophen. In a certain embodiment, the weight ratio of tramadol to acetaminophen in the composition is from about 1:10 to about 1:5.

In certain embodiments, the pharmaceutical compositions of the present invention comprise both tramadol and diclofenac. In a certain embodiment, the weight ratio of tramadol to diclofenac is about 1:4 to 4:1, such as 1:2 to 3:1, and 1:1 to 2.5:1.

In certain embodiments, the pharmaceutical compositions of the present invention comprise both tramadol and aspirin. In a certain embodiment, the weight ratio of tramadol to aspirin is about 1:4 and 4:1, such as between 1:2 and 2:1. In certain embodiments, the pharmaceutical compositions of the present invention comprise both tramadol and carprofen. In a certain embodiment, the weight ratio of tramadol to carprofen is about 3:1 to 10:1.

In certain embodiments, the pharmaceutical compositions of the present invention comprise both tramadol and flupirtine. In a certain embodiment, the weight ratio of tramadol to flupirtine is about 1:1 to 1:5.

In certain embodiments, the pharmaceutical compositions of the present invention comprise both tramadol and codeine or oxycodone. In a certain embodiment, the weight ratio of tramadol to codeine or oxycodone is about 1:20 to about 20:1, such as about 1:2 to about 2:1 and about 1:1 to 2:1.

In certain embodiments, the pharmaceutical compositions of the present invention comprise both tramadol and a NSAID, wherein the weight ratio of tramadol to the NSAID is about 1:1 to about 1:200, from about 1:2 to about 1:200, and about 1:2 to about 1:20.

In certain embodiments, the pharmaceutical compositions of the present invention comprise both tramadol and a calcium channel antagonist (e.g., nimodipine, nicardipine, nifedipine, diltiazem, verapamil, gallopamil, flunarizine, and cinnarizine). In a certain embodiment, the weight ration of tramadol to the calcium channel antagonist is about 200:1 to about 5:1.

In certain embodiments, the tramadol-containing pharmaceutical compositions of the present invention further comprise ketoprofen, cyproheptadine (serotonin antagonist), prozosin (α-1-adrenoceptor antagonist), clonidine (α-2-adrenoceptor agonist), clomipramine (selective inhibitor of serotonin neuronal uptake), or xylamine (selective irreversible inhibitor of norepinepherine uptake).

In certain embodiments, the pharmaceutical compositions of the present invention comprise glucosamine and an analgesic, such as a NSAID. Exemplary NSAIDs include, but are not limited to, aspirin; phenylbutazone, oxyphenbutazone, antipyrine, aminopyrine, dipyrone and apazone; indomethacin; sulindac; fenamates such as mefenamic, meclofenamic, flufenamic, tolfenamic and etofenamice acids; aryl acetic acid and propionic acid compounds such as 2-(p-isobutylphenyl)propionic acid (ibuprofen); alphamethyl-4-(2-thienylcarbonyl)benzene acetic acid (suprofen); 4,5-diphenyl-2-oxazole propionic acid (oxprozin); rac-6-chloro-alphamethyl-carbazole-2-acetic acid (carprofen); 2-(3-phenyloxyphenyl)-propionic acid, particularly the calcium salt dihydrate thereof (fenoprofen and fenoprofen calcium); 2-(6-methoxy-2-naphthyl)propionic acid (naproxen); 4-(1,3-dihydro-1-oxo-2H-isoindol-2-yl)-α-methylbenzene acetic acid (indoprofen); 2-(3-benzoylphenyl)propionic acid (ketoprofen); and 2-(2-fluoro-4-biphenylyl) propionic acid (flurbiprofen) and 1-5-(4-methylbenzoyl)-1H-pyrrole-2-acetic acid (tolmetin). Additional exemplary NSAIDs are compounds within the class including sodium 5-(4-chlorobenzoyl)-1,4-dimethyl-1H-pyrrole-2-acetate dihydrate (zomepirac sodium); 4-hydroxy-2-methyl-N-(2-pyridyl-2H-1,2-benzothiazine-3-carboxamide-1,1-dioxide (piroxicam); 2',4'-difluoro-4-hydroxy-3-biphen-ylcarboxylic acid (diflunisal) or 1-isopropyl-7-methyl-4-phenyl-2 (1H)-quinozolinone (proquazone), and Cox-2 inhibitors such as rofecoxib and celecoxib.

In certain embodiments, the weight ratio of glucosamine to the analgesic in the above pharmaceutical compositions is from about 1:10 to about 100:1, such as from about 1:1 to about 20:1, and about 1:2 to about 10:1.

In certain embodiments, the glucosamine-containing pharmaceutical compositions of the present invention further comprise ibuprofen, diclofenac, tramadol, or acetaminophen. In certain embodiments, the weight ratio of glucosamine to ibuprofen, diclofenac, tramadol, or acetaminophen is from about 1:10 to about 100:1, such as from about 1:1 to about 20:1, and about 1:2 to about 10:1.

In certain embodiments, the pharmaceutical composition of the present invention comprises glucosamine (e.g., glucosamine hydrochloride and glucosamine sulfate), hydrolyzed collagen, and a bioflavanol (e.g., proanthocyanidin, leucocyanidin, pcynogenol, and those extracted from grape seeds, pine bark or turmeric root).

B. Wax-Like Agents

The compositions of the present invention also comprise a wax-like agent that is a pharmaceutically acceptable material capable of forming, together with the active ingredient and spheronizing agent, spherical or non-spherical pellets, and providing sustained release of the active ingredient.

A "wax-like agent," as used herein, refers to a natural, semi-synthetic or synthetic material that is plastic (i.e., malleable) at normal ambient temperatures (i.e., 20-25° C.), has a melting point above 40° C., is very slightly soluble, practically insoluble, or insoluble in water (e.g., having a water-solubility lower than about 1:5000 (w/w)), and is composed of an ester of a fatty alcohol and saturated and unsaturated fatty acid(s), saturated and unsaturated fatty acid glyceride (mono-, di- or triglyceride), hydrogenated fat, hydrogenated vegetable oil, cholesterol, hydrocarbon, hydrophobic polymer having a hydrocarbon backbone, hydrophilic polymer having a hydrocarbon backbone, or a combination of one or more of the above-listed compounds.

A wax-like agent, as used herein, includes commonly known wax, such as animal and insect waxes (e.g., beeswax, Chinese wax, shellac wax, spermaceti wax, lanolin wax), vegetable waxes (e.g., bayberry wax, candelilla wax, carnauba wax, castor wax, esparto wax, Japan was, jojoba oil, ouricury wax, rice bran wax), mineral waxes (e.g., ceresin waxes, montan wax extracted from lignite and brown coal, ozocerite, peat waxes), petroleum waxes (e.g., paraffin wax, microcrystalline wax), and synthetic waxes (e.g., polyethylene waxes, Fischer-Tropsch waxes, chemically modified waxes (e.g., esterified or saponified waxes), substituted amide waxes, and polymerized α-olefins). In certain embodiments, the wax is an ester of ethylene glycol and two fatty acids.

The term "pharmaceutically acceptable," as used herein, refers to being compatible with other ingredients of the composition and not deleterious to the recipient thereof.

In certain embodiments, the wax-like agent is thermoplastic with a melting point above 40° C. (e.g., above 45° C.), and below 120° C. (e.g., below 110° C.), including any value between 40° C. and 120° C. In certain embodiments, the wax-like agent has a melting point in a range formed by any two values between 40° C. and 120° C., such as between 50° and 100° C.

To meet the desire for sustained release, the wax-like agent should be substantially non-degradable and insoluble in gastrointestinal fluids under the relevant time frame (e.g., for 10-12 hours when used in composition that provides sustained release for twice per day administration) and at least under the initial release phase (e.g., the first hour, the first two hours, or the first three hours).

In certain embodiments, the wax-like agent is hydrogenated vegetable oils, such as hydrogenated cottonseed oil, partially hydrogenated cottonseed oil, hydrogenated soybean oil, partially hydrogenated soybean oil, and stearyl alcohol.

In certain embodiments, the wax-like agent is present in the composition in an amount of at least about 1%, 2%, 3%, 4%, 5%, 6%, 7%, 8%, 9%, or 10% of the total weight of the composition. In certain embodiments, the wax-like agent is present in an amount of at most about 15%, 20%, 25%, 30%, 35%, 40%, 45%, or 50% of the total weight of the composition. In certain embodiments, the wax-like agent is present in the range of from about 1% to about 40%, such as from about 1% to about 30%, from about 5% to about 40%, from about 5% to about 40%, or any other range between any one of the above-noted minimum amount and any one of the above-noted maximum amount, w/w relative to the total weight of the composition.

C. Spheronizing Agent

The compositions of the present invention further comprise a spheronizing agent that is a pharmaceutically acceptable material capable of forming, together with the wax-like sustained release agent and active ingredient, spherical and non-spherical pellets.

A "spheronizing agent," as used herein, refers to an agent that together with an active ingredient and a wax-like agent, forms a cohesive plastic mass that may be subsequently spheronized to produce spherical pellets or fragmented to form non-spherical pellets.

In certain embodiments, the spheronizing agent is microcrystalline cellulose, such as the product sold under the tradename "AVICEL™." Other exemplary spheronizing agents include sodium carboxymethylcellulose, pregelatinized starch (e.g., pregelatinized corn starch). In certain embodiment, the spheronizing agent is a combination of microcrystalline cellulose and pregelatinized starch.

In certain embodiments, the spheronizing agent (e.g., microcrystalline cellulose or a combination of microcrystalline cellulose and pregelatinized starch) is present in the composition in an amount of at least about 1%, 2%, 3%, 4%, 5%, 6%, 7%, 8%, 9%, or 10% of the total weight of the composition. In certain embodiments, the spheronizing agent is present in an amount of at most about 11%, 12%, 13%, 14%, 16%, 18%, 20%, 25%, 30%, 35%, 40%, 45%, or 50% of the total weight of the composition. In certain embodiments, the spheronizing agent is present in the range from about 5% to about 40%, such as about 5% to about 20%, from about 8% to about 15%, or from about 9% to about 12%, or any other range between any one of the above-noted minimum amount and any one of the above-noted maximum amount, w/w relative to the total weight of the composition.

D. Sustained Release

The composition of the present invention provides sustained release of the active ingredient.

The term "sustained release," as used in describing the present invention, refers to the release of the active ingredient more slowly than that from an immediate release dosage form. The term may be used interchangeably with "slow-release," "controlled release," or "extended release." The sustained release property of a composition is typically measured by an in vitro dissolution method and confirmed by an in vivo blood concentration-time profile (i.e., a pharmacokinetic profile).

The term "immediate release dosage forms" refers to release forms wherein at least 75% of the active ingredient is released or dissolved within about one-half hour after administration. Such immediate release dosage forms include tablets, capsules, multiparticulates, powders for oral suspension and sachets of an active ingredient. Examples of immediate release dosage forms include, but are not limited to, commercially available various glucosamine tablet and capsule products as described herein in Example 3.

In certain embodiments, the pharmaceutical compositions of the present invention a 2-phase release profile, where the first phase releases 10-60% of the active ingredient in about 1 hour and the second phase releases the rest of the active ingredient, in a nearly linear fashion, for at least about 2, 3, 4, 5, 6, 7, 8, 9, 10, 11, 12, 14, 16, 18, 20, 22, or 24 hours. A pharmaceutically active agent is released in a "nearly linear" fashion for a specified period of time if the release rate of the agent does not change more than 20% during any hour within the specified period of time.

In certain embodiments, the composition has an in vitro dissolution rate measured by standard USP basket method according to Example 3 of: about 10% to about 60% of the active ingredient released after 1 hour; about 20% to about 70% of the active ingredient released after 2 hours; about 30% to about 80% of the active ingredient released after 4 hours; about 40% to about 90% of the active ingredient release after 8 hours; and about 50% to about 100% of the active ingredient release after 12 hours. In certain embodiments, the active ingredient is glucosamine or a pharmaceutically acceptable salt thereof.

In certain embodiments, the composition has an in vitro dissolution rate measured by standard USP basket method according to Example 3 of: about 0% to about 30% after 2 hours; about 5% to about 35% after 4 hours, about 10% to about 40% after 8 hours; about 15% to about 45% after 16 hours; about 20% to about 50% after 24 hours. In certain embodiments, the active ingredient is tramadol or a pharmaceutically acceptable salt thereof.

In certain embodiments, the composition has an in vitro dissolution rate measured by standard USP basket method according to Example 3 of at most about 20%, 30%, 40%, 50%, 60%, 70%, 80%, or 90% of the active ingredient released after 2, 3, 4, 5, 6, 7, 8, 9, 10, 12, 14, 16, 18, 20, 22, or 24 hours.

In certain embodiments, the pharmaceutical composition of the present invention, upon oral administration to a human or non-human patient in need thereof, provides release of its active ingredient at such a rate that the blood level of the active ingredient in the patient is maintained within the therapeutic range (i.e., at or above minimum effective concentration (MEC) but below toxic levels) for at least about 8, 9, 10, 11, 12, 13, 14, 15, 16, 17, 18, 19, 20, 21, 22, 23, 24, 36, 48, 72, 96, 120, 144, or 168 hours.

The MEC of a pharmaceutically active agent of interest in a human or non-human patient may be determined using appropriate techniques known in the art (see, e.g., Grond et al., British Journal of Clinical Pharmacology 48: 254-7, 1999; and Lehmann et al., Clinical Journal of Pain 6: 212-20, 1990 for determining the MEC of tramadol in humans).

In certain embodiments, the composition of the present invention, when administered orally to a patient in need thereof at the equivalent daily dose of an immediate release formulation, provides a plasma concentration of its active ingredient at or above its minimum effective concentration for a period of time at least about the same as, or about 2, 3, 4, or 5 times of, that of the immediate release formulation administered at a daily standard dose (i.e., the daily dose according to the official product description for the formulation or the dose approved by a regulatory authority (e.g., the U.S. FDA) for the formulation).

E. Physical Form—Pellets

In certain embodiments, the composition of the present invention is in the form of pellets.

The term "pellets" refers to small particles with approximately uniform shapes and sizes. A "small particle" refers to a particle of which diameter, length, height, width, or the like is at most 10 mm (e.g., at most 2, 3, 4, 5, 6, 7, 8, or 9 mm). Small particles have approximately uniform sizes if the diameter, length, height, width, or the like of the smallest particle is at least about one half of the average diameter, length, height, width, or the like of the particles and if the diameter, length, height, width, or the like of the largest particle is at most about twice the average diameter, length, height, width, or the like of the particles.

In certain embodiments, the composition of the present invention is in the form of spherical pellets. The term "spherical pellet" refers to pellets, beads, particles, spheroids or the like that are of round or about round shape (i.e., having or approaching the shape of a small sphere).

In certain embodiments, the spherical pellets have a smooth surface texture. Such physical characteristics lead to excellent flow properties, improved "mouth feel," ease of swallowing and ease of uniform coating, if required.

In certain embodiments, the average size (i.e., the average diameter) of the spherical pellets according to this invention may be about 0.1 mm to about 3 mm, including any range formed by any two values between about 0.1 mm and about 3 mm, such as from about 0.5 mm to about 2 mm, or from 0.5 mm to about 1.5 mm. In certain embodiments, the average size of the spherical pellets is about 1 mm. In certain embodiments, the average size of the spherical pellets is at least about 0.2, 0.4, 0.5, 0.6, 0.8, 1, 1.2, 1.4, or 1.5 mm.

In certain embodiments, the sizes of the spherical pellets according to this invention vary within a range of at most about 5%, 10%, 15%, or 20%. In other words, in certain embodiments, the diameters of the spherical pellets according to this invention vary within a range of at most about 5%, 10%, 15%, or 20%. Narrow size variations provide pellets with sufficient spherical homogeneity so that they can conveniently be coated for identification, stability, taste masking, delayed release or sustained or controlled release applications. Additionally, the narrow size variations allow such pellets to have a coating of homogeneous thickness.

In certain embodiments, the size distribution of the spherical pellets may vary in a statistical manner. For example, the size distribution may be in a bell-shaped curve wherein about 90% or about 95% of the number of pellets are within a size range that varies between about 10% to about 20% of the average sizes mentioned above.

In certain embodiments, the composition of the present invention may be in the form of non-spherical pellets (i.e., in the form other than spherical pellets), such as cylindrical pellets. In certain embodiments, the cylindrical pellets may a height from about the same to about 2-3 times of the cylinder diameter. In certain embodiments, the average cylinder diameter is about 0.1 mm to about 3 mm, including any range formed by any two values between about 0.1 mm and about 3 mm, such as from about 0.5 mm to about 2 mm, or from 0.5 mm to about 1.5 mm. In certain embodiments, the average cylinder diameter of the cylindrical pellets is about 1 mm. In certain embodiments, the heights of the non-spherical pellets are about the same.

The pellets according to the invention have low water content. In particular embodiments, the water contents in the pellets is lower than about 5%, 4%, 3%, or 2% of the total weight of the dry pellets.

F. Additional Ingredients and Coating

Optionally, the composition of the present invention may comprise one or more pharmaceutically acceptable inactive ingredients, including binders, antioxidants, and colorants.

Suitable binders include water-soluble hydroxyalkyl celluloses such as hydroxypropyl cellulose, hydroxypropyl methylcellulose (HPMC), sodium carboxymethylcellulose sodium (CMC), or water insoluble polymers, such as pregelatinized starch (e.g., STARCH 1500™ by Colorcon), acrylic polymers or copolymers, or alkyl celluloses such as ethyl cellulose.

Suitable antioxidants include butylated hydroxyanisole (BHA), butylated hydroxytoluene (BHT), vitamin E or ascorbyl palmitate.

Suitable colorants may be selected from any FD&C pigments, dyes or lakes.

In certain embodiments, these other ingredients may be present in the pellets at most about 30%, 20%, 10%, or 5% of the total weight of the dry pellets.

In certain embodiments, the composition of the present invention provides sustained release of an active ingredient without the need of a sustained release barrier coating. In other words, the matrix of the pellets alone is sufficient in providing sustained release of the active ingredient.

The term "sustained release barrier coating" refers to a coating on a dosage form (e.g., spherical or non-spherical pellets) that substantially slows the release of the active ingredient of the dosage form. More specifically, the presence of a sustained release barrier coating on a dosage form reduces the in vitro dissolution rate of the active ingredient within the first two hours (measured by the method disclosed herein) at least by about 50%.

Uncoated sustained release pellets are preferred over coated pellets for lower manufacturing cost and scale-up complexity. A typical sustained release barrier coating for pellets comprises water-insoluble polymers such as ethylcellulose, which is usually applied in an organic solvent or in a proprietary aqueous dispersion (e.g. SURELEASE™ by Colorcon). The organic coating system requires expensive fireproof or explosion-proof equipment and facility and environmental protection measures. The proprietary aqueous dispersion systems are of generally high cost, and because of the greatly increased surface area, pellets need a much high amount of coating on a weight basis compared to tablets. For example, a typical sustained release coating weight for a tablet is about 1-5% of the total weight of the coated tablets whereas pellets would need as high as 20-50% of the total weight of the coated pellets to achieve the same sustained release property (again due to the greater surface area for the pellets). The cost of a proprietary aqueous coating dispersion can therefore become a serious limitation of manufacturing feasibility of a sustained release pellet products. Moreover, pellet coating is normally performed using a fluid bed coater, which is more costly to purchase and to operate than pan coaters conventionally used for tablets.

Another reason to prefer sustained release matrix pellets over coated pellets is the risk of dose dumping. This phenomenon occurs when there are undesired openings or defects in the coating, which may be caused during manufacturing or by the patient while handling the dosage form, or by non-voluntary chewing on it. Small openings or cracks in the coating mantle causes contact of the interior with body fluids setting a catastrophic release of the active causing a serious safety concern.

In certain embodiments, the composition of the present invention is not coated with a sustained release barrier coating. Nevertheless, other functional coatings such as taste masking, color barrier (such as for identification), or moisture barrier (such as for improving stability or shelf life) may be applied to the sustained release pellets of this invention. In another example where a non-sustained release coating may be needed is the active ingredient may be too aggressive to the stomach or other parts of the gastrointestinal system or may be prone to decomposition by gastric juices. In such instances, the active ingredient needs to be kept separated from environmental factors by a suitable technique such as enteric-coating, e.g., by coating the pellets with a layer of polymers that is insoluble at the acidic gastric environment and dissolves only in intestines.

In certain embodiments, although not required, a sustained release barrier coating may be applied to the pellets of the present invention. The presence of the sustained release barrier coating further slows the release of the active ingredient in the pellets.

Suitable sustained release coating materials include water-insoluble waxes and polymers such as polymethacrylates (e.g., the EUDRAGIT™ polymers) or water insoluble celluloses, such as alkyl celluloses (e.g., ethylcellulose). Optionally, water-soluble polymers such as polyvinylpyrrolidone or water-soluble celluloses such as hydroxypropylmethyl-cellulose or hydroxypropylcellulose may be included. Further components that may be added are water-soluble agents such as polysorbate. In certain embodiment, a suitable plasticizer may also be added. In certain embodiment, the coating material sold under the trade name SURELEASE™ (Colorcon), which is a dispersion of ethylcellulose, may be used to form a coating on the pellets of the present invention.

G. Exemplary Formulations

Unless otherwise provided, the exemplary formulations described in this subsection may comprise any active ingredient, especially one or more of those specifically described above. In addition, such exemplary formulations are in the form of pellets and provide sustained release of the active ingredient (e.g., having an in vitro dissolution rate of the active ingredient measured by standard USP basket method of at most about 90% of the active ingredient released after 2 hours) without requiring the presence of a sustained release barrier coating on the pellets.

In certain embodiments, the composition of the present invention in the form of pellets comprises: (a) from about 5% to about 90% of an active ingredient; (b) from about 5% to about 40% of a wax-like agent; and (c) from about 5% to about 40% of a spheronizing agent.

In certain embodiments, the composition of the present invention in the form of pellets comprises: (a) from about 45% to about 85% of an active ingredient; (b) from about 5% to about 30% of a wax-like agent; and (c) from about 5% to about 30% of a spheronizing agent.

In certain embodiments, the composition of the present invention in the form of pellets comprises: (a) from about 50% to about 75% of an active ingredient; (b) from about 10% to about 30% of a wax-like agent; and (c) from about 5% to about 20% of a spheronizing agent.

In certain embodiments, the composition of the present invention in the form of pellets comprises: (a) from about 60% to about 65% of an active ingredient; (b) from about 10% to about 30% of a wax-like agent; and (c) from about 5% to about 20% of a spheronizing agent. In certain embodiments, the composition comprises: (a) from about 45% to about 85% of an analgesic or a pharmaceutically acceptable salt thereof; (b) from about 5% to about 30% of hydrogenated vegetable oil (e.g., hydrogenated cottonseed oil); (c) from about 5% to about 20% of microcrystalline cellulose; and (d) from about 1% to about 10% pregelatinized starch.

In certain embodiments, the composition comprises: (a) from about 45% to about 85% of a dietary supplement or a pharmaceutically acceptable salt thereof; (b) from about 5% to about 30% of hydrogenated vegetable oil (e.g., hydrogenated cottonseed oil); (c) from about 5% to about 20% of microcrystalline cellulose; and (d) from about 1% to about 10% pregelatinized starch.

In certain embodiments, the composition comprises: (a) from about 45% to about 85% of an antiviral agent or a pharmaceutically acceptable salt thereof; (b) from about 5% to about 30% of hydrogenated vegetable oil (e.g., hydrogenated cottonseed oil); (c) from about 5% to about 30% of microcrystalline cellulose; and (d) from about 1% to about 10% pregelatinized starch.

In certain embodiments, the composition comprises: (a) from about 45% to about 85% of an anti-infective agent or a pharmaceutically acceptable salt thereof, (b) from about 5% to about 30% of hydrogenated vegetable oil (e.g., hydrogenated cottonseed oil), (c) from about 5% to about 30% of microcrystalline cellulose, and (d) from about 1% to about 10% pregelatinized starch.

In certain embodiments, the composition comprises: (a) from about 45% to about 85% of an antacid, (b) from about 1% to about 30% of hydrogenated vegetable oil (e.g., hydrogenated cottonseed oil), (c) from about 5% to about 30% of microcrystalline cellulose, and (d) from about 1% to about 10% pregelatinized starch.

In certain embodiments, the composition comprises: (a) from about 45% to about 90% of a high-dose pharmaceutically active agent, (b) from about 5% to about 40% of hydrogenated vegetable oil (e.g., hydrogenated cottonseed oil), (c) from about 5% to about 40% of microcrystalline cellulose, and (d) from about 1% to about 10% pregelatinized starch.

In certain embodiments, the composition comprises: (a) from about 45% to about 85% of an insect growth regulator or a pharmaceutically acceptable salt thereof; (b) from about 5% to about 30% of hydrogenated vegetable oil (e.g., hydrogenated cottonseed oil); (c) from about 5% to about 30% of microcrystalline cellulose; and (d) from about 1% to about 10% pregelatinized starch.

In certain embodiments, the composition comprises: (a) from about 60% to about 65% of tramadol or a pharmaceutically acceptable acid-addition salt thereof (e.g., tramadol hydrochloride); (b) from about 15% to about 30% of hydrogenated vegetable oil (e.g., hydrogenated cottonseed oil); and (c) from about 5% to about 15% of microcrystalline cellulose.

In certain embodiments, the composition comprises: (a) from about 60% to about 65% of glucosamine or a pharmaceutically acceptable acid-addition salt thereof (e.g., glucosamine hydrochloride); (b) from about 15% to about 30% of hydrogenated vegetable oil (e.g., hydrogenated cottonseed oil); and (c) from about 5% to about 15% of microcrystalline cellulose.

In certain embodiments, the composition comprises: (a) from about 60% to about 65% of azithromycin or a pharmaceutically acceptable acid-addition salt thereof (e.g., azithromycin hydrochloride); (b) from about 15% to about 30% of hydrogenated vegetable oil (e.g., hydrogenated cottonseed oil); and (c) from about 5% to about 15% of microcrystalline cellulose.

In certain embodiments, the composition comprises: (a) from about 60% to about 65% of acyclovir or valacyclovir; (b) from about 15% to about 30% of hydrogenated vegetable oil (e.g., hydrogenated cottonseed oil); and (c) from about 5% to about 15% of microcrystalline cellulose.

In certain embodiments, the composition comprises: (a) from about 45% to about 85% of a combination of aluminum hydroxide and magnesium hydroxide in a 3:1, 2:1, 1:1, 1:2, or 1:3 ratio, (b) from about 5% to about 20% of hydrogenated vegetable oil (e.g., hydrogenated cottonseed oil), (c) from about 5% to about 15% of microcrystalline cellulose, and (d) about 1 to about 10% of pregelatinized starch.

In certain embodiments, the composition comprises: (a) from about 40% to 65% of aluminum hydroxide, (b) from about 20% to about 30% magnesium hydroxide, (c) from about 5% to about 15% of hydrogenated vegetable oil (e.g., hydrogenated cottonseed oil); and (d) about 5% to about 15% of microcrystalline cellulose, and (e) about 1 to about 10% of pregelatinized starch.

In certain embodiments, the composition comprises: (a) from about 50% to 75% of sodium phosphate tribase, (b) from about 10% to 30% of hydrogenated vegetable oil (e.g., hydrogenated cottonseed oil), (c) from about 5% to about 15% of microcrystalline cellulose, and (d) about 1% to about 10% of pregelatinized starch.

In certain embodiments, the present invention provides a mixture of one of the two compositions described above in this subsection that contain both aluminum hydroxide and magnesium hydroxide in the form of pellets with the composition described above in this subsection that contains sodium phosphate tribase. In certain embodiments, the weight ratio of the composition that contains both aluminum hydroxide and magnesium hydroxide to the composition that contains sodium phosphate tribase is about 9:1.

II. Dosage Forms

In another aspect, oral dosage forms that comprise the compositions disclosed herein are provided.

The term "oral dosage form" refers to a device that collectively delivers, by oral ingestion, the desired amount of an active ingredient, to achieve a desired dose of the active ingredient. Typically, the oral dosage form is a powder for oral suspension, a unit dose packet or sachet, a tablet, or a capsule.

In certain embodiments, the pellets of this invention may be mixed with a vehicle and packaged in a container such as a screw cap bottle. Prior to dosing, the mixture is added with water or another liquid and shaken to form an "oral suspension." In this oral suspension, the pellets containing the active ingredient may be (a) completely suspended in the vehicle, or (b) partially suspended in the vehicle and partially in solution with the vehicle.

The term "vehicle" refers to a mixture of pharmaceutically acceptable ingredients put together to facilitate the suspension of pellets and improve the taste of an oral suspension. A vehicle useful in this invention may contain suspending agents, anticaking agents, fillers, sweeteners, flavorants, colorants, and/or lubricants.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include colloidal silicon oxide and lactose.

Other conventional excipients may be employed in the compositions of this invention, including those excipients well-known in the art. Generally, excipients such as pigments, lubricants, sweeteners, flavorants, and so forth may be used for customary purposes and in typical amounts without adversely affecting the properties of the compositions.

In certain embodiments, the dosage form may be packaged in a bottle, packet, pouch, sachet, or capsule.

In certain embodiments, the dosage form comprises the active ingredient at a dose of at least about 1, 2, 3, 4, 5, 6, 7, 8, 9, or 10 gram per dose.

In certain embodiments, the invention provides unitary dosage forms that comprise tramadol hydrochloride pellets as described herein in an amount so that the dosage forms contain an effective amount of tramadol hydrochloride. In certain embodiments, such dosage forms may contain from about 10 mg to about 100 mg tramadol hydrochloride per unit, such as from about 15 mg to about 75 mg of tramadol hydrochloride per unit, or from about 25 mg to about 65 mg of tramadol hydrochloride per unit.

In certain embodiments, the invention provides unitary dosage forms that comprise glucosamine hydrochloride pellets as described herein in an amount such that the dosage forms contain an effective amount of glucosamine hydrochloride. In certain embodiments, such dosage forms may contain from about 1,000 mg to about 10,000 mg glucosamine hydrochloride per unit, such as from about 1,500 mg to about 2,500 mg of glucosamine hydrochloride per unit for a human patient, or from about 5,000 mg to about 50,000 mg of glucosamine hydrochloride per unit for an equine patient.

In certain embodiments, the invention provides unitary dosage forms that comprise azithromycin or a pharmaceutical salt thereof pellets as described herein in an amount such that the dosage forms contain an effective amount of azithromycin. In certain embodiments, such dosage forms may contain from about 1,000 mg to about 3,000 mg azithromycin per unit, such as from about 1,500 mg to about 2,500 mg of azithromycin per unit, or about 2,000 mg of azithromycin per unit.

In certain embodiments, the mixture of the pellets of the present invention and a vehicle may be mixed with water to form an oral suspension. In certain other embodiments, other liquids may be used instead of water, such as coffee, tea, milk, and various juices. In certain embodiments, the mixture of water mixed and other excipients, including surfactants, thickeners, suspending agents, and the like, may be used to prepare an oral suspension.

Depending upon the solid-to-liquid ratio, the sustained release pellets dosage form may also be in the form of a paste, slurry or suspension.

In certain embodiments, the dosage form is for single dose use. "Single dose," as used herein, refers to administering only one dose of an active ingredient in the full course of therapy.

In certain embodiments, the dosage form, upon oral administration to a patient in need thereof, provides a plasma concentration of the active agent in the patient at or above its minimum effective concentration for at least about 2, 4, 6, 8, 10, 12, 14, 16, 18, 20, 24, 36, 48, 72, 96, 120, 144, or 168 hours.

In certain embodiments, the dosage form, upon oral administration to a patient in need thereof, provides a plasma concentration of the active agent in the patient at or above its minimum effective concentration for a period of time that is at least about 2, 3, 4, or 5 times of that of an immediate release formulation administered at a standard dose.

In certain embodiments, the dosage form is suitable for administration to a patient in need thereof at, or no more than, once or twice per day, once per two, three, four, five, six, seven days, once per one, two, three, or four weeks, or once per treatment.

III. Methods of Making Compositions

In another aspect, the present invention provides a method for making the compositions and dosage forms described herein.

For example, in one aspect, the present application provides a method for making spherical or non-spherical pellets comprising (i) an active ingredient; (ii) a wax-like agent; and (iii) a spheronizing agent, the method comprising: (a) preparing a mixture of the active ingredient, the wax-like agent, the spheronizing agent, and a liquid; (b) extruding said mixture to obtain an extrudate; (c) spheronizing the extrudate to form spherical pellets or fragmenting the extrudate to form non-spherical pellets; (d) drying the spherical pellets; and (e) heating the dry pellets to a temperature higher than the melting point of the wax-like agent.

In certain embodiments, a method for making sustained release spherical pellets of the present invention is provided, comprising:

(i) mixing dry powder components comprising an active ingredient, a wax-like sustained releasing agent, a spheronizing agent and other optional ingredients with a liquid to form a homogenous and evenly wetted mass, (ii) extrudating the wet mass into cylindrical "spaghetti like" strands ("extrudates"), (iii) spheronizing the extrudates, which fragments the strands into short cylinders and roll-forms them into spheres, (iv) drying the spheres, and (v) heating the dry spheres at a temperature exceeding the melting point of the wax-like sustained release agent.

In certain related embodiments, a method for making sustained release spherical pellets of the present invention comprises steps (i) to (iv) as described above, but not step (v) as described above.

In certain embodiments, spherical pellets may be produced by adding water to a dry blend of an active ingredient, a wax-like agent, a spheronizing agent, and other optional ingredients and extruding the thus formed wet mass through a small orifice (typically approx. 1 mm). Then the extruded material is placed into a spheronizer where it is spun at high speed. During this step, the extrudates break and round into pellets, the size being determined by the size of the extrusion orifice.

To produce extrudates suitable for subsequent spheronization, the wet mass need have the proper cohesiveness and plasticity to undergo plastic deformation and flow through the orifice as cylindrical extrudates. Furthermore, the subsequent spheronization process requires the extrudates to be friable enough to break into short lengths, but sufficiently plastic for the short lengths to form into spheres and not so wet or sticky that the spheres agglomerate and become oversized, or stick to the spin plate of the spheronizer.

The ratios of the wax-like agent to the spheronizing agent as well as the water content in the wet extrudates may be adjusted to produce wet extrudates suitable for spheronization. In certain embodiments, the ratio of the wax-like agent to the spheronizing agent is in a range from about 3:1 to about 1:14 by weight (including any range formed by any two values between about 3:1 to about 1:14), the water content in the wet extrudates in the range of about 30% to about 90% (including any range formed by any two values between about 30% and about 90%) based on the weight of the wet mass.

In certain embodiments, the wet mass is produced with an organic solvent or its mixture with water. The organic solvent may be selected based on its ability to form a spheronizable wet mass, to render a low toxicity, and to be removed by the drying steps to low residual level. To select a safe solvent, Class 2 and Class 3 Solvents as listed in the US FDA "Guidance for Industry, Q3C Impurities: Residual Solvents" may be referenced. Examples of such solvents include:

Class 2 Solvents

| Solvent | PDE (mg/day) | Concentration Limit (ppm) |
|---|---|---|
| Acetonitrile | 4.1 | 410 |
| Chlorobenzene | 3.6 | 360 |
| Chloroform | 0.6 | 60 |
| Cyclohexane | 38.8 | 3,880 |
| 1,2-Dichloroethene | 18.7 | 1,870 |
| Dichloromethane | 6.0 | 600 |
| 1,2-Dimethoxyethane | 1.0 | 100 |
| N,N-Dimethylacetamide | 10.9 | 1,090 |
| N,N-Dimethylformamide | 8.8 | 880 |
| 1,4-Dioxane | 3.8 | 380 |
| 2-Ethoxyethanol | 1.6 | 160 |
| Ethyleneglycol | 6.2 | 620 |
| Formamide | 2.2 | 220 |
| Hexane | 2.9 | 290 |
| Methanol | 30.0 | 3,000 |
| 2-Methoxyethanol | 0.5 | 50 |
| Methylbutyl ketone | 0.5 | 50 |
| Methylcyclohexane | 11.8 | 1,180 |
| N-Methylpyrrolidone | 5.3 | 530 |
| Nitromethane | 0.5 | 50 |
| Pyridine | 2.0 | 200 |
| Sulfolane | 1.6 | 160 |
| Tetrahydrofuran | 7.2 | 720 |
| Tetralin | 1.0 | 100 |
| Toluene | 8.9 | 890 |
| 1,1,2-Trichloroethene | 0.8 | 80 |
| Xylene[1] | 21.7 | 2,170 |

Class 3 Solvents

Acetic acid
Acetone
Anisole
1-Butanol
2-Butanol
Butyl acetate
tert-Butylmethyl ether
Cumene
Dimethyl sulfoxide
Ethanol
Ethyl acetate
Ethyl ether
Ethyl formate
Formic acid
Heptane
Isobutyl acetate
Isopropyl acetate
Methyl acetate
3-Methyl-1-butanol
Methylethyl ketone
Methylisobutyl ketone
2-Methyl-1-propanol
Pentanel
1-Pentanol
1-Propanol
2-Propanol
Propyl acetate In certain embodiments, mixtures of propylene glycol and water, ethanol and water, isopropanol and water are used to produce the wet mass.

In certain embodiments, the wax-like agent content may be in the range of about 5% to about 50% of the weight of the dry pellets (i.e., pellets produced by performing steps (i) to (v) or by performing steps (i) to (iv) if step (v) is not performed). In certain embodiments, the wax-like agent is at most about 30% or 25% of the weight of the dry pellets. In certain embodiments, the wax-like agent is about 20% of the weight of the dry pellets.

In order for a wax-like sustained release agent to provide a sustained release of the active ingredient in the pellet form, the pellets need be dried and heated at a temperature exceeding the melting point of the wax-like sustained release agent. The present invention may utilize a fluid-bed processor to dry the pellets at about 40° C. (hot air temperature) to remove the majority amount of the water ("the first stage of drying") and heat the dry pellets at a temperature which is about 15 to 20° C. higher than the melting point of the wax-like agent (e.g., 75° C. hot air temperature) to remove the tightly bound water and to impart the desired sustained release property to the pellets ("the second stage of drying").

The drying/heating process may be applied in two consecutive steps; the first stage of drying is primarily to remove water and to cause the pellet to sufficiently harden to allow for more rigorous heating in the second stage of drying. A lower temperature (about 40° C., which is below the melting point of the wax-like agent) is usually sufficient for the drying purpose and is preferred for the stability of the active ingredient. The drying time of the first stage may vary from 10 minutes to several hours depending upon the batch size and efficiency of the dryer. The end point for the first stage of drying is water content of less than about 5% to about 10% relative to the total weight of the pellets after the first stage of drying.

The second stage of drying further reduces the water content in the pellets to less than about 2% relative to the total weight of the resulting pellets. In certain embodiments, the second stage of drying is performed at a temperature about 15° C. to about 20° C. higher than the melting point of the wax-like agent to remove the tightly bound water. The drying time of the second stage drying may vary from 15 minutes to several hours depending upon the batch size and efficiency of the dryer. An even higher temperature may be applied so long that it does not cause deformation or agglomeration of pellets or thermal degradation of the active or other ingredients in the pellets. In addition to lowering the water content to less than about 2% relative to the total weight of the resulting pellets, the end point for the second stage drying is also for the pellets to reach their targeted sustained release profile.

Not wishing to be bound by any theory, the second stage of drying, which resembles a thermal annealing treatment, is believed to cause a partial melting of wax-like sustained release agent in the pellets to allow for more intimate incorporation and embedment of the active ingredient in the matrix of the wax-like agent without any significant deformation or agglomeration of the pellets. The melting and congealing of the wax-like sustained release agent may also help sealing the pores in the pellets due to the removal of water and thus reduce the surface area of the pellets. Pellets prepared by the same method described herein but without the second drying step exhibited significantly faster drug release (see, Example 17).

In certain embodiments, the drying process is one continuous step where the temperature is ramped from about room temperature to about 15° C. to about 20° C. above the melting point of the wax-like sustained release agent in a timed program.

In certain embodiments, the drying and heating of pellets may be performed in a fluid bed process, convection or microwave oven.

In other embodiments, a method for making sustained release non-spherical pellets of the present invention is provided, comprising:

(i) mixing dry powder components comprising an active ingredient, a wax-like sustained releasing agent, spheronizing agent and optional other ingredients with a liquid to form a homogenous and evenly wetted mass, (ii) extrudating the wet mass into cylindrical "spaghetti like" strands ("extrudates"), (iii) fragmenting the extrudates into pellets of short cylindrical lengths, (iv) drying the pellets, and (v) heating the dry pellets at a temperature exceeding the melting point of the wax-like sustained release agent.

In certain related embodiments, a method for making sustained release non-spherical pellets of the present invention comprises steps (i) to (iv) as described above, but not step (v) as described above.

Above steps (i), (ii), (iv), and (v) for making non-spherical pellets may be performed similar to those described above for making spherical pellets.

As to step (iii), in certain embodiments, a planetary mixer (e.g., a Hobart mixer) equipped with a wire mixing head (e.g., "egg beater") or a cutter may be used to break the wet extrudates into cylindrical pellets the height of which may vary from about the same to about 2 to 3 times of cylinder diameter.

IV. Methods of Using Compositions and Dosage Forms

In one aspect, the present invention provides methods for using the pharmaceutical compositions and dosage forms described herein. Such pharmaceutical compositions may be used for treating or preventing (i.e., reducing the risk of) diseases or disorders that the pharmaceutically active agents in the compositions are suitable for treating or preventing.

The diseases or disorders include, but are not limited to, pains, joint weakness, bacterial or viral infections, lipid disorder, diabetes, vitamin or mineral deficiency, gastrointestinal ulcer or other disorders, asthma, and parasite infestation.

In certain embodiments, the present invention provides a method for reducing pain comprising administering orally to a patient in need thereof a pharmaceutical composition or dosage form as described herein that comprises an effective amount of an analgesic or a pharmaceutically acceptable salt thereof.

In certain embodiments, the present invention provides a method for reducing pain comprising administering orally to a patient in need thereof a pharmaceutical composition or dosage form as described herein that comprises an effective amount of tramadol, tramadol HCl or another pharmaceutically acceptable salt.

In certain embodiments, the present invention provides a method for reducing joint discomfort or increasing joint flexibility comprising administering orally to a patient in need thereof a pharmaceutical composition or dosage form as described herein that comprises an effective amount of glucosamine, glucosamine sulfate, glucosamine HCl or another pharmaceutically acceptable salt.

In certain embodiments, the present invention provides a method for reducing joint discomfort or increasing joint flexibility comprising administering orally to a patient in need thereof a pharmaceutical composition or dosage form as described herein that comprises an effective amount of glucosamine HCl and chondroitin sulfate.

In certain embodiments, the present invention provides a method for reducing pain or fever that comprises administering orally to a patient in need thereof a pharmaceutical composition or dosage form as described herein comprising an effective amount of acetaminophen.

In certain embodiments, the present invention provides a method for treating or preventing (i.e., reducing the risk of) seizure or reducing neuropathic pain that comprises administering orally to a patient in need thereof a pharmaceutical composition or dosage form as described herein comprising an effective amount of gabapentin.

In certain embodiments, the present invention provides a method for lowering blood sugar level comprising administering orally to a patient in need thereof a pharmaceutical composition or dosage form as described herein that comprises an effective amount of metformin hydrochloride.

In certain embodiments, the present invention provides a method for treating or preventing dietary deficiency that comprises administering orally to a patient in need thereof a pharmaceutical composition or dosage form as described herein comprising an effective amount of dietary supplement.

In certain embodiments, the present invention provides a method for treating or preventing viral infection that comprises administering orally to a patient in need thereof a pharmaceutical composition or dosage form as described herein comprising an effective amount of an anti-viral agent.

In certain embodiments, the present invention provides a method for treating or preventing bacterial infection that comprises administering orally to a patient in need thereof a pharmaceutical composition or dosage form as described herein comprising an effective amount of an anti-infective agent or a pharmaceutically effective salt thereof.

In certain embodiments, the present invention provides a method for treating or preventing bacterial infection that comprises administering orally to a patient in need thereof a pharmaceutical composition or dosage form as described herein comprising an effective amount of an antibiotic.

In certain embodiments, the present invention provides a method for treating or preventing a gastrointestinal ulcer or disorder that comprises administering orally to a patient in need thereof a pharmaceutical composition or dosage form as described herein comprising an effective amount of an antacid agent.

In certain embodiments, the method for treating or preventing gastrointestinal ulcer or disorder comprises administering orally to a patient in need thereof a mixture of a composition that comprises aluminum hydroxide and magnesium hydroxide described herein and a composition that comprises sodium phosphate tribase described herein. In certain embodiments, the ratio of the total weight of aluminum hydroxide and magnesium hydroxide to sodium phosphate tribase is about 9;1. In certain embodiments, the present invention provides a method for treating or preventing parasite and/or pest infestation that comprises administering orally to a patient in need thereof a pharmaceutical composition or dosage form as described herein comprising an effective amount of an insect growth regulator.

Patients in need of treatment or prevention of a disease or disorder include both human patients (e.g., adult human patients) and non-human patients (e.g., dogs, cats, horses, and other pets or farm animals).

An "effective amount" refers to the amount of a pharmaceutically active agent effective in treating or preventing a disease or disorder. Such amount may be determined by appropriate methods known in the art. For instance, a sufficient amount of an analgesic or analgesics (such as tramadol and acetaminophen) in a pharmaceutical composition of the present invention may be determined using various methods for measuring analgesia, such as those described in U.S. Patent Application Publication No. 20050089558, Collier et al., Br. J. Pharmacol. 32: 295, 1968; D'Amour et al., J. Pharmacol. Exp. Ther. 72: 74, 1941; and Hargreaves et al., Pain 32: 77, 1988.

In certain embodiments, the pharmaceutical composition or dosage form may be combined with food or animal feed before administration.

The following examples are provided without any intent to limit the scope of the instant invention.

EXAMPLES

Example 1

Preparation of Sustained Release Spherical Pellets of Glucosamine Hydrochloride

A dry blend of 325 g of glucosamine hydrochloride (by Pharmore), 100 g of hydrogenated cottonseed oil, NF (STEROTEX®, by Abitec Corp.), 45 g of microcrystalline cellulose, NF (AVICEL® by FMC Biopolymers), and 30 g of pregelatinized starch (STARCH 1500® by Colorcon Corp.) was wet massed with approximately 155 g of de-ionized water using a planetary mixer (Hobart) and extruded through a small orifice (1.2 mm) using an Fuji Paudal Multi-Gran model MG-55 extruder with a dome-die screen. The extruded material (extrudates) was placed into a spheronizer (Fuji Paudal Marumerizer QJ-230T-1) where it was spun at 1000 RPM for about 1 to 10 minutes. During this step, the extrudate broke and rounded into pellets, the size of which being determined by the size of the extrusion orifice. The extrudate broke easily and produced round pellets of uniform size, and no sticking was observed in the spheronizer. The wet spherical pellets were placed in open-air area at room temperature for about 16 hours, transferred into a fluid bed dryer (Labline Model 23850), dried at 40° C. for 15 hours and then heated at 75° C. for 15 minutes. The dry pellets were sieved through a 12-mesh sieve to remove large particles and a 32-mesh sieve to remove fine particles. The particles with size between 0.5 mm and 1.8 mm in diameter were collected. The process yielded 96.6% dry pellets. The pellets were spherical in shape with a moisture content of 0.46% w/w.

About 84 milligrams of the resulting spherical glucosamine pellets were weighed out and transferred into a 50 mL volumetric flask, and simulated gastric fluid (USP, without enzymes) was added to the 50-mL volume mark. The content was mixed well and sonicated in a bath sonicator to extract glucosamine from the pellets. The supernatant was removed and injected into an HPLC under the following conditions:
  Column: Hamilton RCX-10, M 250×4.6 mm
  Mobile phase: 10 mM NaOH in water
  Flow: 1.2 mL/min
  Column temperature: 30 deg C.
  Detection wavelength: 215 nm The content of glucosamine hydrochloride in the pellets produced as described above was determined to be 62.2% w/w.

Example 2

Preparation of Sustained Release Non-Spherical (Cylindrical) Pellets of Glucosamine Hydrochloride A dry blend of 3250 g of glucosamine hydrochloride (by Pharmore), 1000 g of hydrogenated cottonseed oil, NF (STEROTEX®, by Abitec Corp.), 450 g of microcrystalline cellulose, NF (AVICEL® by FMC Biopolymers), and 300 g of pregelatinized starch (STARCH 1500® by Colorcon Corp) was wet massed with approximately 1500 g of de-ionized water using a planetary mixer (Hobart) and extruded through a small orifice (1.2 mm) using an Fuji Paudal Multi-Gran model MG-55 extruder with a dome-die screen. The extruded material (extrudate) was placed into a 6-quart mixer (KitchenAid mixer with an egg mixing apparatus) where it was spun at about 1000 RPM for about 1-2 minute. During this step the extrudate broke into small cylindrical pellets (non-spherical), the height of the cylinders being close to the diameter of the extrudate. The extrudate broke easily and produced cylindrical pellets of fairly uniform size and no sticking was observed in the spheronizer. The wet spherical pellets were placed in open-air area at room temperature for about 16 hours, transferred into a fluid bed dryer (Labline Model 23850), dried at 40° C. for 15 hours and then heated at 75° C. for 15 minutes. The dry pellets were sieved through a 12-mesh sieve to remove large particles and a 32-mesh sieve to remove fine particles. The particles with size between 0.5 mm and 1.8 mm in diameter were collected. The process yielded 97.2% dry pellets.

The thus prepared non-spherical pellets were cylindrical in shape with a moisture content of 0.41% w/w and glucosamine hydrochloride content of 65.7% w/w. The pellets were mixed with 0.1% molasses flavor for voluntary consumption by horses.

Example 3

Dissolution Rate

The in vitro dissolution rate of the preparation of Example 1 was measured according to the standard USP Basket Method (Apparatus type 1) using the following conditions:
  Sample size: 1 g pellets per basket
  Speed: 50 RPM
  Medium: Simulated gastric fluid SGF per USP without enzyme Volume: 500 mL/vessel
Temperature: 37° C.
Concentration analysis: HPLC Representative dissolution profiles from spherical and non-spherical pellets are shown in FIG. 1 and the general profile can be described as follows:
About 40% active ingredient released after 1 hour,
About 50% active ingredient released after 2 hours,
About 60% active ingredient released after 4 hours,
About 70% active ingredient released after 8 hours,
About 80% active ingredient released after 12 hours,
About 90% active ingredient released after 18 hours, and
About 100% active ingredient released after 24 hours.

Figure 2:
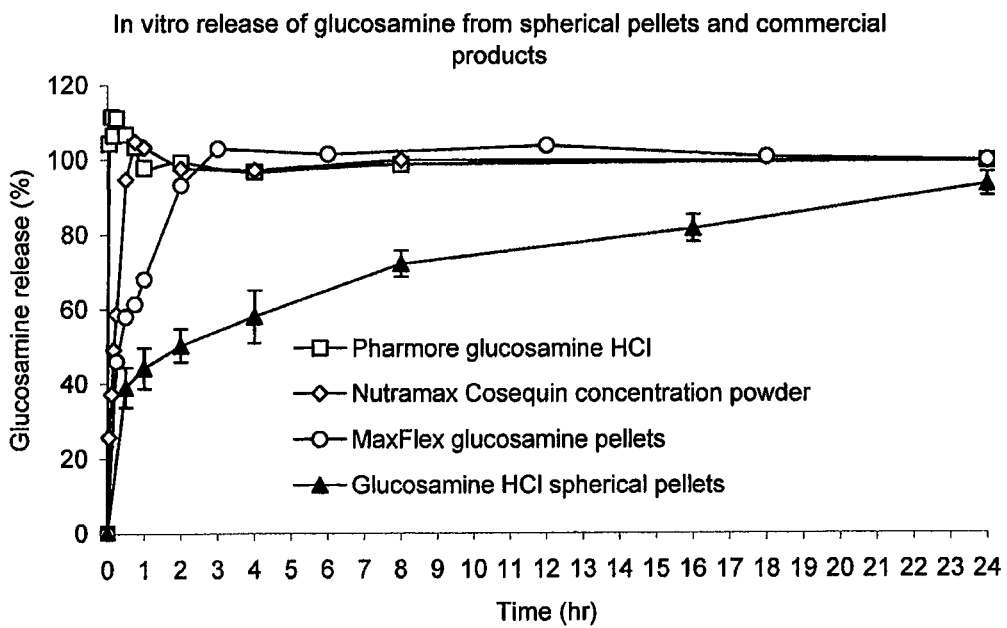
FIG. 2. Comparison of glucosamine in vitro dissolution profiles between the pellets prepared according to Examples 1 and 2 and commercial products.

Other commercially available multiparticulate formulations of glucosamine have also been tested using the same method and results are shown in FIG. 2. The release was completed (100% release) in about or less than 3 hours for the commercial products compared to 24 hours for the pellets prepared according to Example 1.

Example 4

Stability of Active Ingredient in Pellets

Figure 3:
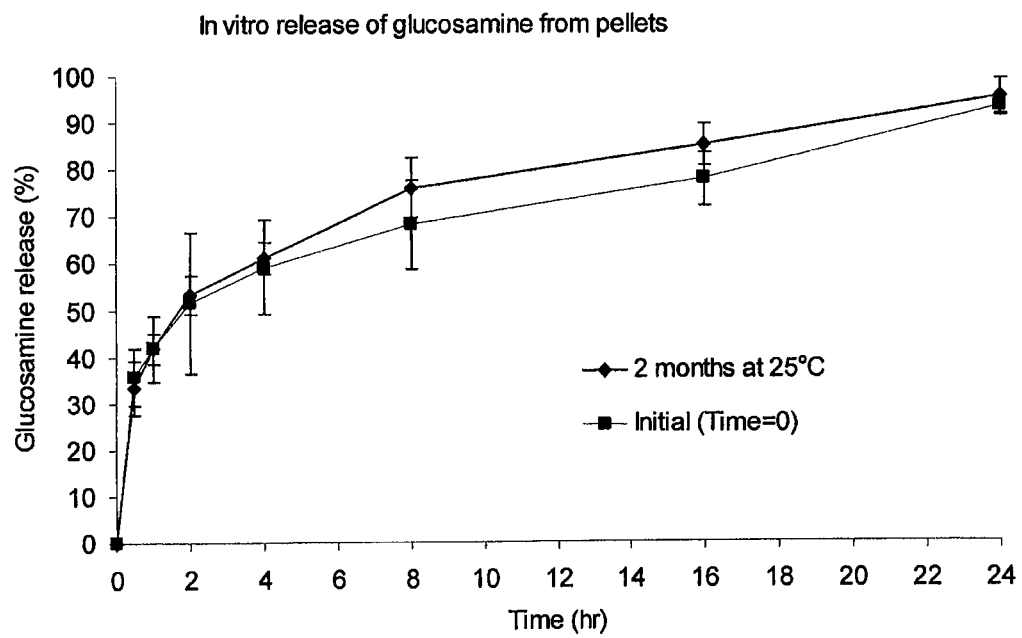
FIG. 3. Dissolution profiles from cylindrical pellets prepared according to Example 2 measured in two months apart.

Glucosamine pellets prepared according to Example 2 were placed in a sealed container and stored at 25° C./60% RH for 2 months. The pellets were tested for contents of active ingredient and dissolution rates using the methods described in Examples 2 and 3. The results of active ingredient contents are represented in table below and dissolution profiles in FIG. 3. The results show that glucosamine is stable in the pellets for at least two months.

|  | Glucosamine HCl Recovered over the Initial Conc. (%) | |
| --- | --- | --- |
|  | Initial | 2 Month |
| Storage | 100 | 98.1 |

Example 5

Figure 4:
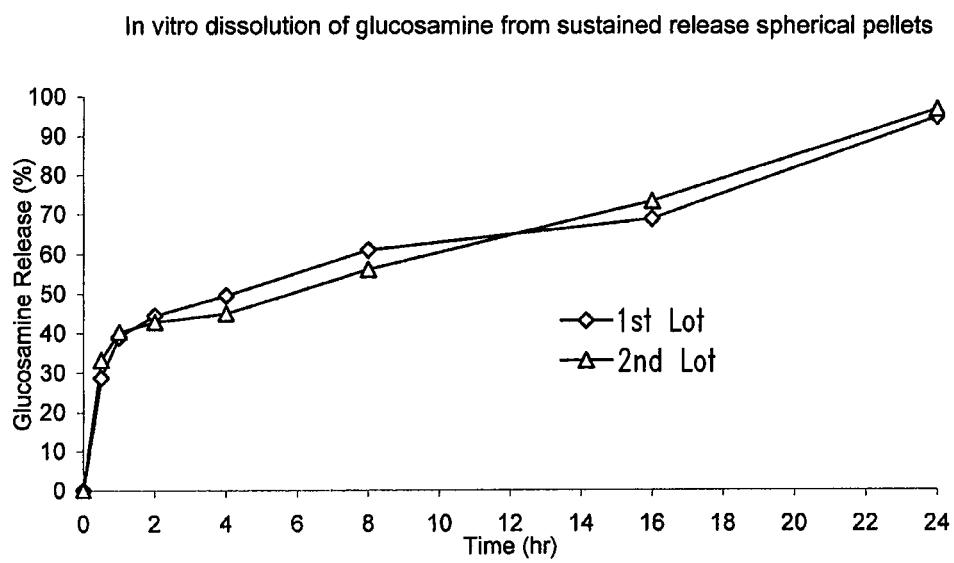
FIG. 4. In vitro dissolution of glucosamine from sustained release spherical pellets containing glucosamine hydrochloride, chondroitin sulfate, calcium ascorbate and manganese sulfate prepared according to Example 5.

Preparation of Sustained Release Spherical Pellets Containing Glucosamine Hydrochloride, Chondroitin Sulfate, Ascorbic Acid and Manganese Sulfate A dry blend of 50 g of glucosamine hydrochloride (by Pharmore), 4.7 g chondroitin sulfate (by Maypro), 1 g calcium ascorbate (by Zila) and 0.3 g manganese sulfate (by Prince Agri), 0.1 g molasses flavor powder (by Gold Coast), 20 g of hydrogenated cottonseed oil, NF (STEROTEX®, by Abitec Corp.), and 24 g of microcrystalline cellulose, NF (AVICEL® by FMC Biopolymers) was wet massed with approximately 30 g of de-ionized water using a planetary mixer (KitchenAid) and extruded through a small orifice (1.2 mm) using an Fuji Paudal Multi-Gran model MG-55 extruder with a dome-die screen. The extruded material (extrudates) was placed into an spheronizer (Fuji Paudal Marumerizer QJ-230T-1) where it was spun at 1500 RPM for about 1 to 2 minutes. During this step, the extrudate broke and rounded into pellets, the size being determined by the size of the extrusion orifice. The extrudate broke easily and produced round pellets of uniform size, and no sticking was observed in the spheronizer. The wet spherical pellets were placed in open-air area at room temperature for about 3 hours, transferred into a fluid bed dryer (Labline Model 23850), dried at 40° C. for 10 hours and then heated at 75° C. for 10 minutes. The thus prepared spherical pellets were spherical in shape with moisture content of 0.46% w/w. The in vitro dissolution profile of glucosamine is shown in FIG. 4.

Example 6

Preparation of Tramadol Hydrochloride Spherical Pellets

A series of spherical pellets containing a highly water soluble tramadol hydrochloride were prepared to contain the following compositions:

| Component/ formulation code | Weight percent based on total solids | | | | | | | |
| --- | --- | --- | --- | --- | --- | --- | --- | --- |
|  | F-8 | F-9 | F-10 | F-11 | F-12 | F-13 | F-15 | F-16 |
| Tramadol HCl | 3.3 | 3.3 | 3.3 | 3.3 | 15.0 | 20.0 | 25.0 | 30 |
| Cation exchange resin | 13.3 | 13.3 | 13.3 | 13.3 | 45.0 | 40.0 | 40.0 | 40 |
| Microcrystalline cellulose | 73.3 | 63.3 | 36.7 | 53.3 | 40.0 | 40.0 | 35.0 | 30 |
| Hydrogenated cottonseed oil | 10.0 | 20.0 | 13.3 | 30 | 0 | 0 | 0 | 0 |

Tramadol HCl was first mixed with cation exchange resin (Amberlite IRP69 by Rohm Haas) and the mixture was suspended and mixed in de-ionized water to allow for the binding of tramadol to the resin. The suspension was wet massed with microcrystalline cellulose and hydrogenated cottonseed oil, extrudated, spheronized, dried and heated according to the method described in Example 1.

Figure 5:
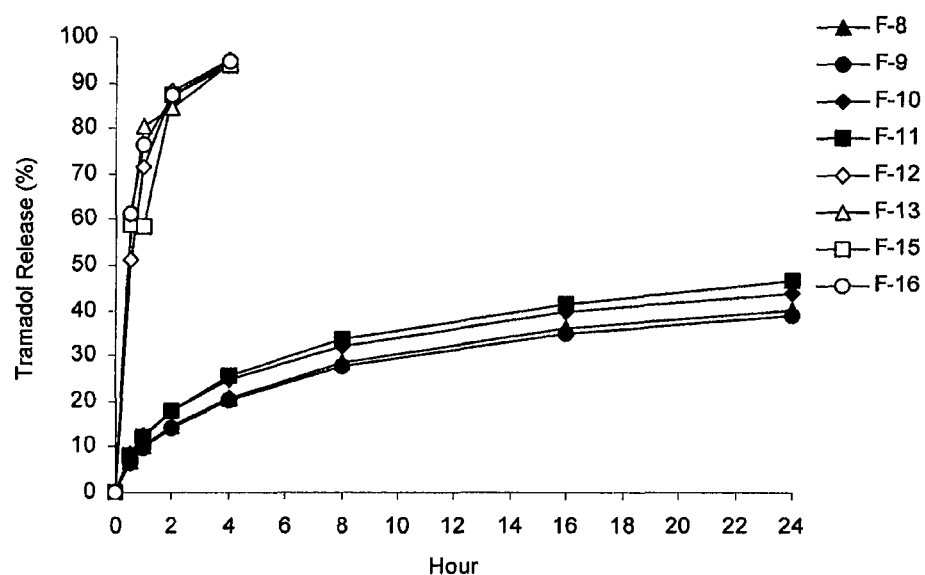
FIG. 5. In vitro dissolution of tramadol from spherical pellets prepared according to Example 6.

In vitro dissolution profiles are shown in FIG. 5. The spherical pellets prepared according to this invention F-8, F-9, F-10 and F-11) exhibited extensively sustained release characteristics with more than 24 release duration observed. Pellets prepared without hydrogenated cottonseed oil (F-11, F-12, F-13, F-15 and F-16), on the other hand, released tramadol in about 4 hours and is regarded inappropriate for once-a-day dosing. This study indicates feasibility of providing a once-a-day formulation for tramadol using the sustained release pellets process and formulation according to this invention. It further demonstrates the necessity of the wax-like agent in such sustained release pellets formulations.

Example 7

Preparation of Azithromycin Sustained Release Spherical Pellets

A dry blend of 100 g of azithromycin, USP (by Polymed), 50 g of hydrogenated cottonseed oil, NF (STEROTEX®, by Abitec Corp.), 28 g of microcrystalline cellulose, NF (AVICEL® by FMC Biopolymers), 0.04 g BHA and 22 g of pregelatinized starch (STARCH 1500® by Colorcon Corp.) was wet massed, extrudated, spheronized, dried and heated according to the method described in Example 1.

The thus prepared pellets were spherical in shape with a moisture content of 0.5% w/w and azithromycin content of 52.3% w/w.

Example 8

Preparation of Azithromycin Spherical Pellets for Oral Suspension

A vehicle was prepared by mixing 946 g sucrose, NF, 3.2 g hydroxypropyl cellulose, NF, 3.3 g xanthan gum, NF, 9.8 g colloidal silicon dioxide, NF, 19.5 g titanium dioxide, USP, 6.9 cherry flavoring powder, and 11.3 g banana flavoring powder.

Four grams of azithromycin pellets prepared according to Example 7 (containing 2 g azithromycin) were mixed with 20 g of the vehicle in a 100 mL plastic bottle to provide a powder blend formulation for oral suspension. This powder blend forms a uniform suspension upon manual shaking after addition of 60 mL water. The thus formed suspension provides pleasing taste and mouth feel and is easy to be swallowed.

The powder blend thus prepared was tested for in vitro dissolution and compared with a commercial sustained release suspension product (ZMAX™, azithromycin extended release for oral suspension by Pfizer) using the method as described in U.S. Pat. No. 6,984,403. ZMAX™ (azithromycin extended release) for oral suspension is a single-dose, liquid antibiotic used to treat certain types of mild to moderate bacterial infections including Acute bacterial sinusitis (ABS) and Community-acquired pneumonia (CAP). ZMAX™ provides a full course of treatment in a single, high dose (i.e., the patient takes just one dose, one time).

Figure 6:
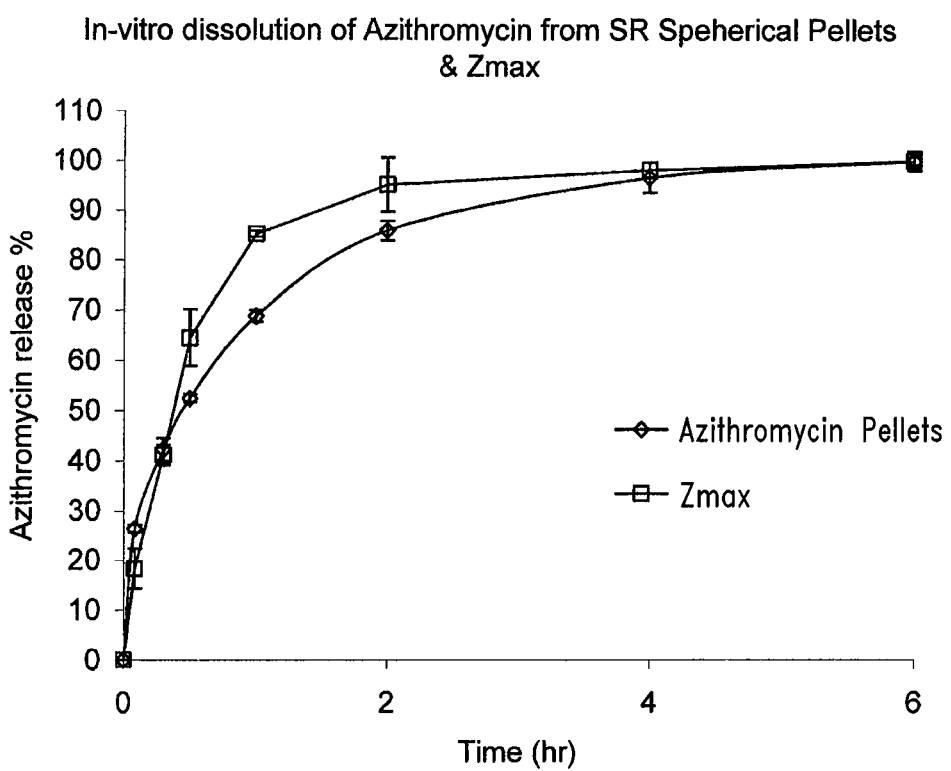
FIG. 6. In vitro dissolution of azithromycin pellets for oral suspension prepared according to Examples 7 and 8 and ZMAX™ by Pfizer performed according to the method described in U.S. Pat. No. 6,984,403.

The results of the in vitro dissolution comparison between the powder blend according to this example and ZMAX™ are shown in FIG. 6. They demonstrate that the sustained release pellets prepared according to this invention is capable of providing a sustained release profile of azithromycin comparable to other extended release suspension, such as ZMAX™, which is prepared using a very different composition and method. It is also indicated that a high dose (2 g or more) can be readily dosed in the powder blend containing spherical pellets as described in this example.

Example 9

Stability of Azithromycin Spherical Pellets for Oral Suspension

Stability of azithromycin in spherical pellets for oral suspension according to Examples 7 and 8 was evaluated by measuring for appearance, pH, moisture content, drug content and purity, and in vitro dissolution of azithromycin. The pellets were packaged with the vehicle (as described in Example 8) in high density polyethylene bottles, and the bottles were stored in 25° C./60% RH and 40° C./75% RH stability chambers.

The drug content in the azithromycin spherical pellets for oral suspension was measured using an HPLC method under the following conditions:

Column: a 5-micron reverse-phase C-18 column with 4.6 mm diameter and 100 mm length
Mobile phase A: 0.05% trifluoroacetic acid in water
Mobile phase B: 0.05% trifluoroacetic acid in acetonitriles
Column temperature: 40° C.
Flow rate; 0.7 mL/min
Detection: 205 nm The tables below show the stability test results. The results indicated that the azithromycin spherical pellets for oral suspension prepared according to this invention are stable at least for 12 months.

| Storage Condition | Azithromycin concentration (mg) | | | | | |
|---|---|---|---|---|---|---|
| | Initial | 1 Month | 2 Month | 3 Month | 6 Month | 12 Month |
| 25° C./60% RH | 83.0 | 84.9 | 84.0 | 84.7 | 84.3 | 83.2 |
| 40° C./75% RH | 83.0 | 79.7 | 85.0 | 82.0 | 80.9 | Not measured |

| Storage Condition | Azithromycin recovery over the Initial Conc. (%) | | | | | |
|---|---|---|---|---|---|---|
| | Initial | 1 Month | 2 Month | 3 Month | 6 Month | 12 Month |
| 25° C./60% RH | 100 | 102.3 | 101.2 | 102.0 | 101.5 | 100.2 |
| 40° C./75% RH | 100 | 96.1 | 102.4 | 98.8 | 97.4 | Not measured |

| Storage Condition | pH of Azithromycin SR pellets | | | | | |
|---|---|---|---|---|---|---|
| | Initial | 1 Month | 2 Month | 3 Month | 6 Month | 12 Month |
| 25° C./60% RH | 9.06 | 8.83 | 8.92 | 9.08 | 9.33 | 9.35 |
| 40° C./75% RH | 9.06 | 8.84 | 9.09 | 9.16 | 8.94 | Not measured |

| Storage | Moisture level of Azithromycin SR pellets (%) | | | | | |
|---|---|---|---|---|---|---|
| Condition | Initial | 1 Month | 2 Month | 3 Month | 6 Month | 12 Month |
| 25° C./60% RH | 0.44 | 0.48 | 0.63 | 0.69 | 0.56 | 0.51 |
| 40° C./75% RH | 0.44 | 0.76 | 0.62 | 0.68 | 0.52 | Not measured |

| Storage | Appearance of Azithromycin SR pellets | | | | | |
|---|---|---|---|---|---|---|
| Condition | Initial | 1 Month | 2 Month | 3 Month | 6 Month | 12 Month |
| 25° C./60% RH | White, non aggregated, non-sticky | Same | Same | Same | Same | Same |
| 40° C./75% RH | White, non-aggregated, non-stick | Same | Same | Same | Same | Not measured |

Example 10

Preparation of Valacyclovir Sustained Release Spherical Pellets

A dry blend of 100 g of valacyclovir, 50 g of hydrogenated cottonseed oil, NF (STEROTEX®, by Abitec Corp.), 28 g of microcrystalline cellulose, NF (AVICEL® by FMC Biopolymers), 0.04 g BHA and 22 g of pregelatinized starch (STARCH 1500® by Colorcon Corp.) is wet massed with a water-propylene glycol mixture (60:40=v:v), extruded, spheronized, dried and heated according to the method described in Example 1 to form dry spherical pellets. Alternatively, the dry blend is wet massed, extruded, fragmented, dried and heated according to the method described in Example 2 to form dry non-spherical pellets. The pellets thus prepared can be further mixed to a vehicle similar to the one described in Example 8 to obtain a powder blend for oral suspension. Such suspension may be used for treatment or prophylaxis of viral infections by a single-dose regimen, i.e., one dose (1 g or more valacyclovir) per treatment.

Example 11

Preparation of Antacid Sustained Release Spherical Pellets

A dry blend of 853.3 g of aluminum hydroxide, USP, 426.7 g magnesium hydroxide, 80 g of hydrogenated cottonseed oil, NF (STEROTEX®, by Abitec Corp.), 144 g of microcrystalline cellulose, NF (AVICEL® by FMC Biopolymers), and 96 g of pregelatinized starch (STARCH 1500® by Colorcon Corp) was wet massed, extrudated, spheronized, dried and heated according to the method described in Example 1 to form dry spherical pellets. The thus prepared pellets were spherical in shape with a moisture content of 2.6% w/w.

Another dry blend of 65 g of sodium phosphate tribasic, 20 g of hydrogenated cottonseed oil, NF (STEROTEX®, by Abitec Corp.), 9 g of microcrystalline cellulose, NF (AVICEL® by FMC Biopolymers), and 6 g of pregelatinized starch (STARCH 1500® by Colorcon Corp) was wet massed, extrudated, spheronized, dried and heated according to the method described in Example 1 to form dry spherical pellets. The thus prepared pellets were spherical in shape.

The mixture of pellets was prepared by mixing well 9 weight parts of dry spherical pellets containing aluminum hydroxide and magnesium hydroxide and 1 weight part of dry spherical pellets containing sodium phosphate tribase and was tested in horses for antacid activities.

Example 12

Preparation of Vitamin-Mineral Sustained Release Spherical Pellets

A dry blend of 100 g of a vitamin (such as vitamin A, B, C, D, and E), a mineral (such as calcium, iron and zinc), or a mixture thereof, 50 g of hydrogenated cottonseed oil, NF (STEROTEX®, by Abitec Corp.), 28 g of microcrystalline cellulose, NF (AVICEL® by FMC Biopolymers), 0.04 g BHA and 22 g of pregelatinized starch (STARCH 1500® by Colorcon Corp.) is wet massed, extruded, spheronized, dried and heated according to the method described in Example 1 to form dry spherical pellets. Alternatively, the dry blend is wet massed, extruded, fragmented, dried and heated according to the method described in Example 2 to form dry non-spherical pellets. The pellets thus prepared can be mixed to a flavor such as molasses powder or a vehicle similar to the one described in Example 8 to obtain a powder blend for oral suspension. The said powder blend may be provided to animals such as horses for voluntary consumption or to human patients as an oral suspension. Such suspension may be used for a prolonged supply of vitamins and minerals to a human or animal subject in need of such supplement by a single-dose regimen, i.e., one dose (1 g or more of a vitamin, mineral or mixture thereof) per day.

Example 13

Preparation of Ursodiol Sustained Release Spherical Pellets

A dry blend of 100 g of ursodiol, 50 g of hydrogenated cottonseed oil, NF (STEROTEX®, by Abitec Corp.), 28 g of microcrystalline cellulose, NF (AVICEL® by FMC Biopolymers), 0.04 g BHA, and 22 g of pregelatinized starch (STARCH 1500® by Colorcon Corp.) is wet massed, extruded, spheronized, dried and heated according to the method described in Example 1 to form dry spherical pellets.

Alternatively, the dry blend is wet massed, extruded, fragmented, dried and heated according to the method described in Example 2 to form dry non-spherical pellets. The pellets thus prepared can be mixed to a flavor such as molasses powder or a vehicle similar to the one described in Example 8 to obtain a powder blend for oral suspension. The said powder blend may be provided to human patients as an oral suspension. Such suspension is intended to dissolve gallstones in patients and for treatment for primary biliary cirrhosis, and other cholestatic diseases, including fat liver by a single-dose regimen, i.e., one dose (1 g or more of ursodiol) per day.

Example 14

Preparation of Metformin Sustained Release Spherical Pellets

A dry blend of 100 g of metformin or its pharmaceutical salt, alone or in combination with another antidiabetic drug selected from sulfonylurea class (e.g., glyburide), thiazoidinedione class (e.g., rosiglitazone, pioglitazone), or DPP-4 inhibitors (e.g., Januvia), 50 g of hydrogenated cottonseed oil, NF (STEROTEX®, by Abitec Corp.), 28 g of microcrystalline cellulose, NF (AVICEL® by FMC Biopolymers), 0.04 g BHA, and 22 g of pregelatinized starch (STARCH 1500® by Colorcon Corp.) is wet massed, extruded, spheronized, dried and heated according to the method described in Example 1 to form dry spherical pellets. Alternatively, the dry blend is wet massed, extruded, fragmented, dried and heated according to the method described in Example 2 to form dry non-spherical pellets. The pellets thus prepared can be mixed to a flavor such as molasses powder or a vehicle similar to the one described in Example 8 to obtain a powder blend for oral suspension. The powder blend may be provided to human patients as an oral suspension. Such suspension may be used for treatment of diabetes by a single-dose regimen, i.e., one dose (1 g or more of active drug) per day.

Example 15

Reparation of Polyene Phosphatidylcholine Sustained Release Spherical Pellets

A dry blend of 100 g of polyene phosphatidylcholine, 50 g of hydrogenated cottonseed oil, NF (STEROTEX®, by Abitec Corp.), 28 g of microcrystalline cellulose, NF (AVICEL® by FMC Biopolymers), 0.04 g BHA and 22 g of pregelatinized starch (STARCH 1500® by Colorcon Corp) is wet massed, extruded, spheronized, dried and heated according to the method described in Example 1 to form dry spherical pellets. Alternatively, the dry blend is wet massed, extruded, fragmented, dried and heated according to the method described in Example 2 to form dry non-spherical pellets. The pellets thus prepared are capable of releasing the active agent(s) in a sustained release fashion and can be mixed to a flavor such as molasses powder or a vehicle similar to the one described in Example 8 to obtain a powder blend for oral suspension. The powder blend may be provided to human patients as an oral suspension. Such suspension may be used for lowering elevated hepatic enzyme levels, treatment of liver steatosis or other hepatic disorder by a single-dose regimen, i.e., one dose (1 g or more of active drug) per day.

Example 16

Preparation of Gabapentin Sustained Release Spherical Pellets

A dry blend of 100 g of gabapentin, 50 g of hydrogenated cottonseed oil, NF (STEROTEX®, by Abitec Corp.), 28 g of microcrystalline cellulose, NF (AVICEL® by FMC Biopolymers), 0.04 g BHA and 22 g of pregelatinized starch (STARCH 1500® by Colorcon Corp.) is wet massed, extruded, spheronized, dried and heated according to the method described in Example 1 to form dry spherical pellets. Alternatively, the dry blend is wet massed, extruded, fragmented, dried and heated according to the method described in Example 2 to form dry non-spherical pellets. The pellets can be mixed to a flavor such as molasses powder or a vehicle similar to the one described in Example 8 to obtain a powder blend for oral suspension. The powder blend may be provided to human patients as an oral suspension. Such suspension is intended for treatment of seizure or other neuropathic disorders by a single-dose regimen, i.e., one dose (1 g or more of active drug) per day.

Example 17

Comparison of In Vitro Dissolution of Glucosamine Pellets Processed by Different Heating Conditions An in vitro dissolution test was carried for the pellets prepared according to this invention using a standard UPS dissolution apparatus I (basket). The method is detailed as follow:
  APPARATUS: USP dissolution apparatus I (basket)
  Medium: USP Simulated gastric fluid (without enzymes)
  Medium volume: 500 mL
  Temperature: 37° C.
  Stir: 50 RPM
  Sample volume: 1 mL (without replenishment with fresh medium).
  Each sample was filtered through a 10-micron filter prior to filling into HPLC vial. Typical Sampling time: 0.5, 1, 2, 4, 8, 16 and 24 hours.
  After 24 hours, the remaining pellet mass (soft gel-like) was homogenized in the medium using a mechanical mixer to form a uniform dispersion, which was then filtered through the 10-micron filter and analyzed by HPLC as the "100% release" sample. The in vitro release (%) values in all previous samples (0.5-24 hr) were normalized based on the "100% release" using the following equation: % release=100×(drug conc. in a previous sample)/(drug conc. in the "100% release sample").
  The concentration of a drug in the medium samples was analyzed using a HPLC method as described in detail below.
  An ion-exchange HPLC method with the following conditions was used for glucosamine analysis:
  Column: Hamilton RCX-10
  Mobile Phase: 10 mM NaOH in water, 0.8 micron filtered
  Flow rate: 1.2 mL/min
  Column temp: 30° C.
  Injection: 50 μL
  UV Detection: 209 nm
  Run time: 7 min
  A reverse phase HPLC method with the following conditions was used for tramadol analysis:
  System: An HPLC system capable of performing binary gradient elution and UV detection
  Column: Luna C18 5μ 4.6×250 mm, by Phenomenex Mobile Phase A: 0.1% v/v trifluoroacetic acid in water, 0.8 micron filtered Mobile Phase B: 0.1% v/v trifluoroacetic acid in acetonitrile, 0.8 micron filtered Column temp: 40° C.

Flow rate: 1 mL/min

Injection: 5 µL

UV Detection: 270 nm

Run time: 5 min

Elution: Isocratic at 65% (v/v) Mobile Phase A and 35% (v/v) Mobile Phase B

Figure 7:
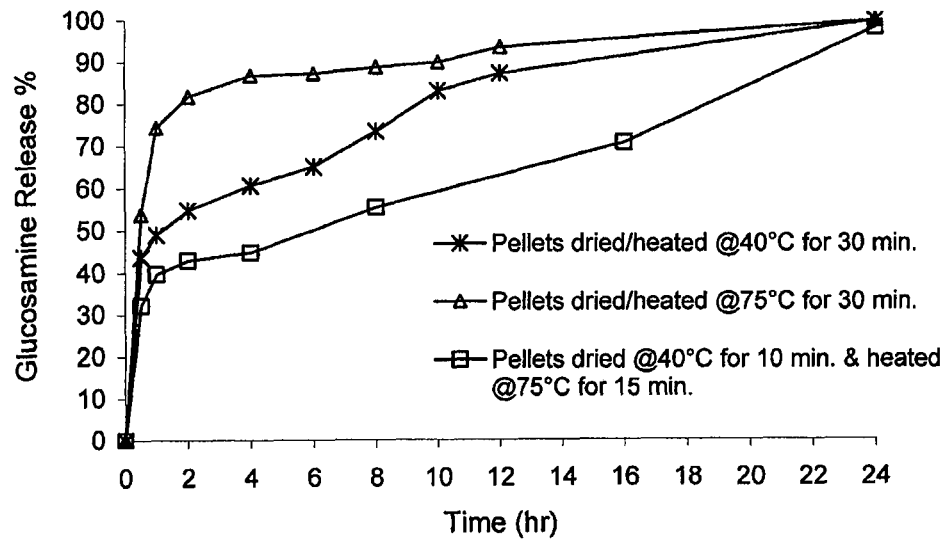
FIG. 7. In vitro dissolution profiles of glucosamine from spherical pellets by different heating conditions prepared according to Example 17.

The in vitro dissolution results from the glucosamine spherical pellets are depicted in FIG. 7. It is apparent that the drying/heating conditions had profound effects of the glucosamine release. The pellets made with the 2 separate drying and heating ("pellets dried at 40° C. and heated at 75° C.") exhibited the desired release profile, i.e., about 40% release in the first hour and the rest in the next 23 hours in near zero-order kinetic (linear). This 2-step dissolution profile is one of the characteristics of the pellets prepared according to certain embodiments of this invention, where the initial fast release of about 40% of the drug load provides a quick onset of action (i.e., a loading dose) and the second phase of the extended release allows for a prolonged action of the drug (i.e., a maintenance dose). Pellets that were either dried/heated in one-step at a 40° C. for 30 minutes or 75° C. for 30 minutes did not provide the same extended release with about 85-90% drug released in about 12 hours. The results of this study indicate that the separate drying at 40° C. for 10 minutes and heating at 75° C. (above the melting point of the wax-like agent) for 15 minutes render the sustained release property of the pellets.

Example 18

Figure 8:
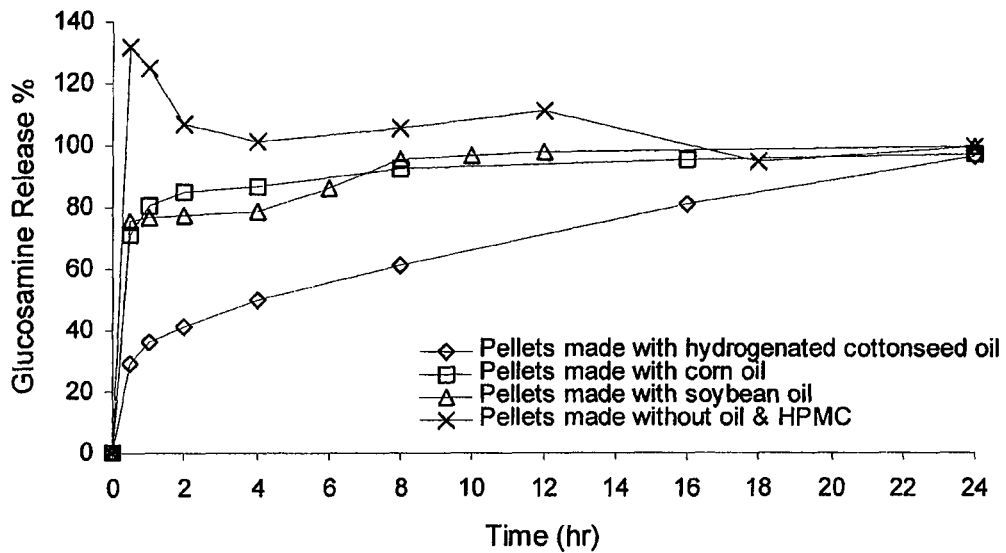
FIG. 8. In vitro dissolution profiles of glucosamine from spherical pellets prepared with various oil according to Example 18.

In Vitro Dissolution of Glucosamine from Pellets Prepared without a Wax-Like Agent Spherical pellets containing glucosamine with non-wax-like oils (corn oil and soybean oil) or hydrogen-forming polymer (hydroxypropy methylcellulose or HPMC) commonly used in sustained release products were prepared using a method similar to what is described in Example 1 and tested using the method for glucosamine analysis according to Example 17. The results show that the non wax-like agents (corn oil, soybean oil or HPMC) did not provide the same sustained release property as a wax-like agent (hydrogenated cottonseed oil). In fact, pellets made without the wax-like agent released about or more than 80% of their drug load in the first hour (FIG. 8).

Example 19

Preparation of Tramadol Hydrochloride Sustained Release Spherical Pellets

Figure 9:
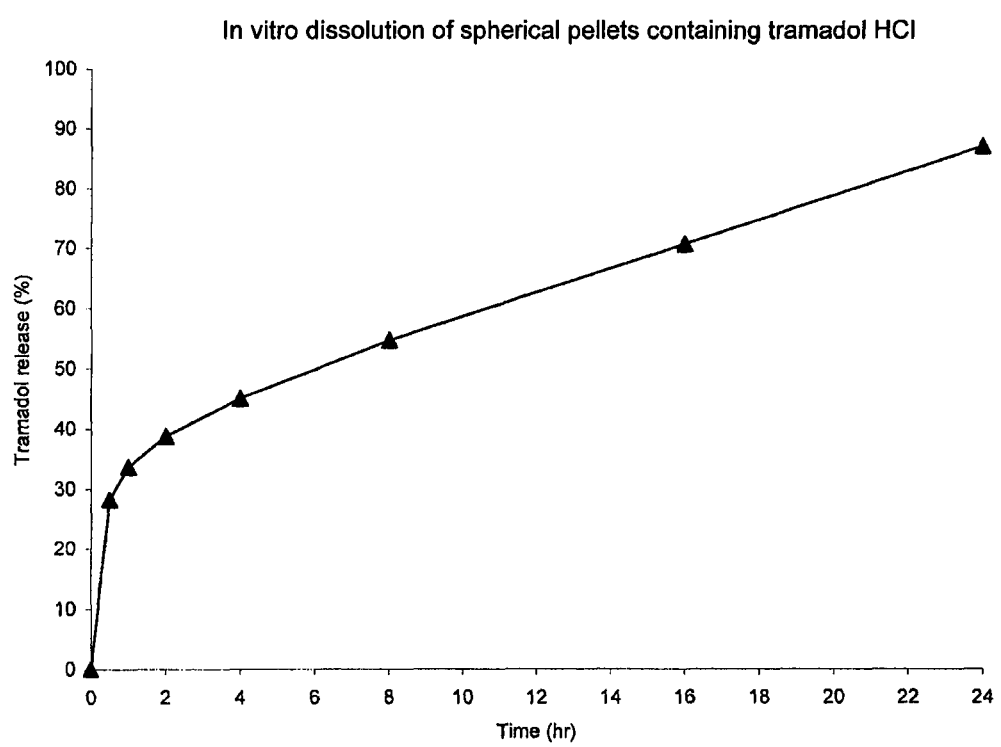
FIG. 9. In vitro dissolution profile of tramadol from spherical pellets prepared according to Example 19.

A dry blend of 750 g of tramadol hydrochloride (Degussa), 750 g of hydrogenated cottonseed oil, NF (STEROTEX®, by Abitec Corp.) and 1000 g of microcrystalline cellulose, NF (AVICEL® by FMC Biopolymers) was wet massed with about 900 gram water, extrudated, spheronized, dried and heated according to the method described in Example 1 to form dry spherical pellets. The thus prepared pellets were spherical in shape with a moisture content of 0.42% w/w. The pellets were tested for in vitro dissolution and exhibited a characteristic 2-phase dissolution profile with an about 35% initial fast release followed by a 24 hour extended release (FIG. 9). These pellets were tested in horses for pharmacokinetic profiles.

Example 20

Pharmacokinetic Study of Tramadol Hydrochloride Sustained Release Spherical Pellets Six healthy adult horses, weighing approximately 600 kg, were administered the tramadol sustained release spherical pellets prepared according to Example 19 at a dosage of 10 mg/kg, orally, as a top dress on feed. Twelve healthy adult horses, weighing approximately 600 kg, were administered the tramadol active at a dosage of 10 mg/kg, orally, as a top dress on feed. After the single oral dose on Day 0, blood samples from all horses were collected at various intervals after dosing and analyzed for tramadol and the main active metabolite, M1.

Figure 10:
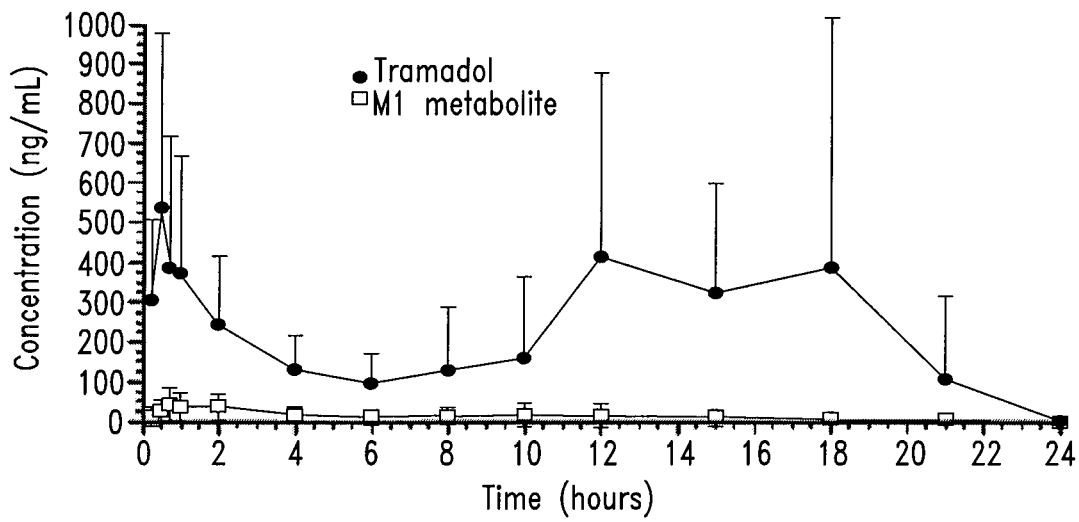
FIG. 10. Pharmacokinetic profiles of tramadol and its main active metabolite, M1, in horses following oral administration of tramadol hydrochloride sustained release spherical pellets.
Figure 11:
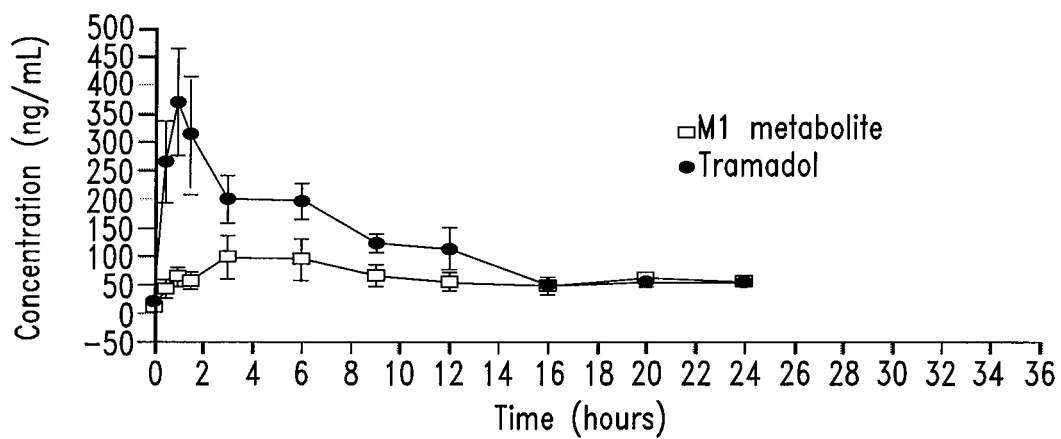
FIG. 11. Pharmacokinetic profiles of tramadol and its main active metabolite, M1, in horses following oral administration of tramadol hydrochloride.

Pharmacokinetic profiles of tramadol and M1 in horses following oral administration of tramadol hydrochloride sustained release spherical pellets (FIG. 10) and following oral administration of unformulated tramadol hydrochloride (FIG. 11) show that tramadol sustained release spherical pellets prepared as described above appears to deliver tramadol at a relevant plasma concentration over an extended period of time compared to non-formulated drug.

Example 21

Antacid Activity Evaluation of Antacid Sustained Release Spherical Pellets

Figure 12:
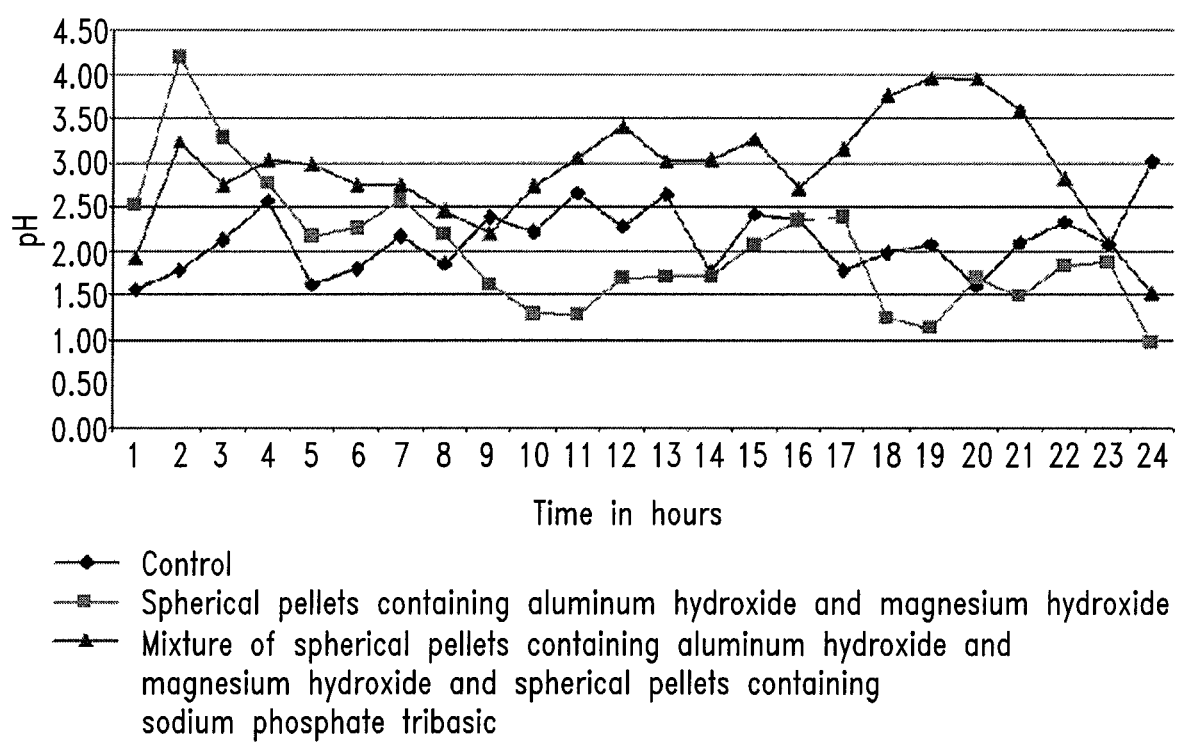
FIG. 12. Horse gastric pH following oral administration of two antacid sustained release spherical pellet formulations: (1) the formulation that contains aluminum hydroxide and magnesium hydroxide prepared according to Example 11, and (2) the 9:1 combination of spherical pellets that contain aluminum hydroxide and magnesium hydroxide and spherical pellets that contain sodium phosphate tribase also prepared according to Example 11.

The objective of this study was to evaluate the buffering capacity of two antacid sustained release spherical pellet formulations on gastric pH in horses. One formulation is the spherical pellets that contain aluminum hydroxide and magnesium hydroxide prepared according to Example 11. The other formulation is a 9:1 combination of spherical pellets that contain aluminum hydroxide and magnesium hydroxide and spherical pellets that contain sodium phosphate tribase according to Example 11. Six horses weighing approximately 500-650 kg and with indwelling pH electrodes were administered the antacid sustained release spherical pellets orally, as a top dress on feed. Baseline gastric pH measurements were compared to measurements at intervals post dosing (FIG. 12). The results show that antacid agents formulated in the sustained release spherical pellets according to Example 11 appear to affect the pH of the stomach for an extended period.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A composition comprising:
   (a) an active ingredient, wherein the active ingredient is glucosamine or a pharmaceutically acceptable salt thereof;

(b) from about 5% to about 40% of a wax-like agent, wherein the wax-like agent is hydrogenated vegetable oil; and (c) from about 5% to about 40% of a spheronizing agent, wherein the ratio of the wax-like agent to the spheronizing agent is in a range from about 3:1 to about 1:14 by weight and; wherein the spheronizing agent is a member selected from the group consisting of microcrystalline cellulose and a combination of microcrystalline cellulose and pregelatinized starch, and wherein the spheronizing agent together with the active ingredient and the wax-like agent form a cohesive plastic mass that is malleable and is subsequently extruded and spheronized;

wherein (i) the composition is in the form of pellets, without a sustained release barrier coating, wherein said pellets have an average diameter of about 0.1 mm to about 3 mm in size and are either spherical or cylindrical in shape; (ii) the composition has an in vitro dissolution rate of the active ingredient measured by standard USP basket method of about 10% to about 60% of the active ingredient released after 1 hour;

about 20% to about 70% of the active ingredient released after 2 hours;

about 30% to about 80% of the active ingredient released after 4 hours;

about 40% to about 90% of the active ingredient released after 8 hours;

about 50% to about 100% of the active ingredient released after 12 hours; and (iii) the in vitro dissolution rate of the active ingredient does not require the presence of a sustained release barrier coating on the pellets.

2. The composition of claim 1, wherein the pellets are spherical.

3. The composition of claim 1, wherein the pellets are cylindrical.

4. The composition of claim 1, comprising: from about 5% to about 90% of the active ingredient, wherein the active ingredient is glucosamine or a pharmaceutically acceptable salt thereof.

5. The composition of claim 1, further comprising one or more inactive ingredients.

6. The composition of claim 5, wherein the one or more inactive ingredient is selected from the group consisting of a binder, antioxidant, or colorant.

7. The composition of claim 5, wherein the one or more inactive ingredients are present at the total concentration from about 0.01% to about 5.0% based on the pellet weight.

8. The composition of claim 1, comprising:
(a) from about 45% to about 85% of glucosamine or a pharmaceutically acceptable salt thereof;
(b) from about 5% to about 30% of hydrogenated vegetable oil;
(c) from about 5% to about 20% of microcrystalline cellulose; and from about 1% to about 10% pregelatinized starch.

9. The composition of claim 1, wherein the pellets are coated.

10. The composition of claim 2, wherein the average diameter of the spherical pellets are about 0.5 mm to about 1.5 mm.

11. The composition of claim 1, wherein the hydrogenated vegetable oil is hydrogenated cottonseed oil.

12. The composition of claim 1, wherein the spheronizing agent is microcrystalline cellulose.

13. A dosage form comprising the composition of claim 1.

14. The dosage form of claim 13, further comprising an inactive ingredient selected from the group consisting of flavorants, suspending agents, anticaking agents, fillers, sweeteners, and lubricants.

15. The dosage form of claim 13, wherein the dosage form further comprises water and is in the form of an oral suspension.

16. The dosage form of claim 13 packaged in a bottle, packet, pouch, sachet, or capsule.

17. The dosage form of claim 13, wherein the dosage form, upon oral administration to a patient in need thereof, provides a plasma concentration of the active agent at or above its minimum effective concentration for at least 12 hours.

18. The dosage form of claim 13, wherein the dosage form, upon oral administration to a patient in need thereof, provides a plasma concentration of the active agent at or above its minimum effective concentration for a period of time that is at least 2 times of that of an immediate release formulation administered at a standard dose.

19. The dosage form according to claim 13, wherein dosage form is suitable for administration to a patient in need thereof once or twice per day.

* * * * *